(12) United States Patent
Larson et al.

(10) Patent No.: US 6,498,951 B1
(45) Date of Patent: Dec. 24, 2002

(54) IMPLANTABLE MEDICAL DEVICE EMPLOYING INTEGRAL HOUSING FOR A FORMABLE FLAT BATTERY

(75) Inventors: Lary R. Larson, Gold Canyon, AZ (US); Walter C. Sunderland, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 49 days.

(21) Appl. No.: 09/687,446

(22) Filed: Oct. 13, 2000

(51) Int. Cl.⁷ .............................................. A61N 1/375
(52) U.S. Cl. ....................................................... 607/36
(58) Field of Search .................... 607/36; 361/517–519, 361/535–537; 206/363; 174/50, 50.5, 50.52, 52.1, 582.3, 52.4, 52.6

(56) References Cited

U.S. PATENT DOCUMENTS

| | | |
|---|---|---|
| 4,374,817 A | 2/1983 | Lehman et al. .............. 423/319 |
| 4,379,459 A | 4/1983 | Stein ..................... 128/419 PG |
| 4,384,585 A | 5/1983 | Zipes ..................... 128/419 D |
| 4,476,868 A | 10/1984 | Thompson ............ 128/419 PG |
| 4,548,209 A | 10/1985 | Wielders et al. ......... 128/419 D |
| 4,556,063 A | 12/1985 | Thompson et al. .... 128/419 PT |
| 4,577,633 A | 3/1986 | Berkovits et al. ..... 128/419 PG |
| 4,587,970 A | 5/1986 | Holley et al. .......... 128/419 PG |
| 4,693,253 A | 9/1987 | Adams .................... 128/419 D |
| 4,726,380 A | 2/1988 | Vollmann et al. ..... 128/419 PG |
| 4,821,723 A | 4/1989 | Baker, Jr. et al. ....... 128/419 D |
| 4,830,006 A | 5/1989 | Haluska et al. ....... 128/419 PG |
| 4,880,005 A | 11/1989 | Pless et al. ............ 128/419 PG |
| 4,949,719 A | 8/1990 | Pless et al. ............. 128/419 D |
| 4,949,730 A | 8/1990 | Cobben et al. ............. 128/775 |
| 5,127,404 A | 7/1992 | Wyborny et al. ........ 128/419 P |
| 5,131,388 A * | 7/1992 | Pless et al. ..................... 607/5 |
| 5,144,949 A | 9/1992 | Olson ................... 128/419 PG |
| 5,158,078 A | 10/1992 | Bennett et al. ....... 128/419 PG |
| 5,199,428 A | 4/1993 | Obel et al. .............. 128/419 C |
| 5,207,218 A | 5/1993 | Carpentier et al. ... 128/419 PG |
| 5,312,453 A | 5/1994 | Shelton et al. ................. 607/19 |
| 5,314,430 A | 5/1994 | Bardy ............................ 607/5 |
| 5,330,507 A | 7/1994 | Schwartz ..................... 607/14 |
| 5,331,966 A | 7/1994 | Bennett et al. ............. 128/696 |
| 5,354,316 A | 10/1994 | Keimel ........................ 607/15 |
| 5,370,669 A | 12/1994 | Daglow et al. ............... 607/36 |
| 5,447,519 A | 9/1995 | Peterson ........................ 607/5 |
| 5,470,345 A | 11/1995 | Hassler et al. |
| 5,545,186 A | 8/1996 | Olson et al. .................. 607/14 |

FOREIGN PATENT DOCUMENTS

| | | |
|---|---|---|
| EP | 0 534 782 A1 | 9/1992 |
| EP | 0 800 843 A1 | 10/1997 |

OTHER PUBLICATIONS

Greatbatch, Wilson, et al Lithium/Carbon Monfluoride (Li/DVx): a New Pacemaker Battery, *Pace*, Nov. 1996 Part II, vol. 19, pp1836–1840.

* cited by examiner

Primary Examiner—Kennedy Schaetzle
Assistant Examiner—Kristen Droesch
(74) Attorney, Agent, or Firm—Girma Wolde-Michael

(57) ABSTRACT

A body implantable medical device (IMD) includes a first shell and a second shell whose outer surfaces are biocompatible. The IMD further includes a battery enclosure defined by a cover and all or a portion of the first shell of the IMD housing. The cover of the battery enclosure is disposed between the inner surfaces of the first and second shells and has a greater rigidity than the first shell. An electrochemical cell, such as a flat liquid electrolyte battery, is provided in the battery enclosure. Electronic circuitry, supported on a flexible wiring substrate, is provided between the inner surface of the second shell and the cover of the battery enclosure. A hermetic seal is provided between the cover of the battery enclosure and all or a portion of the first shell. The hermetic seal is preferably a weld joint, such as a butt, spank or standing edge weld joint.

18 Claims, 25 Drawing Sheets

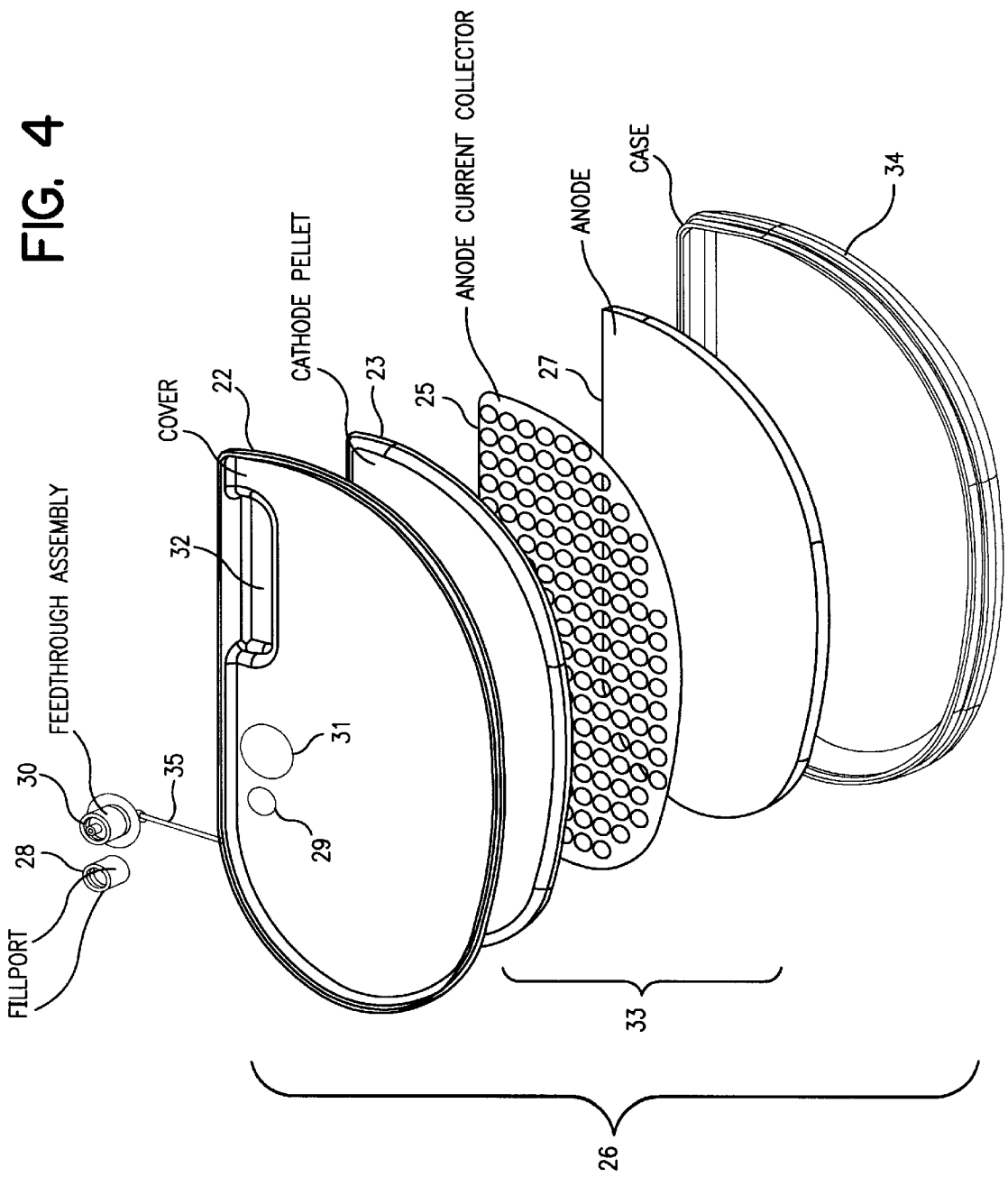

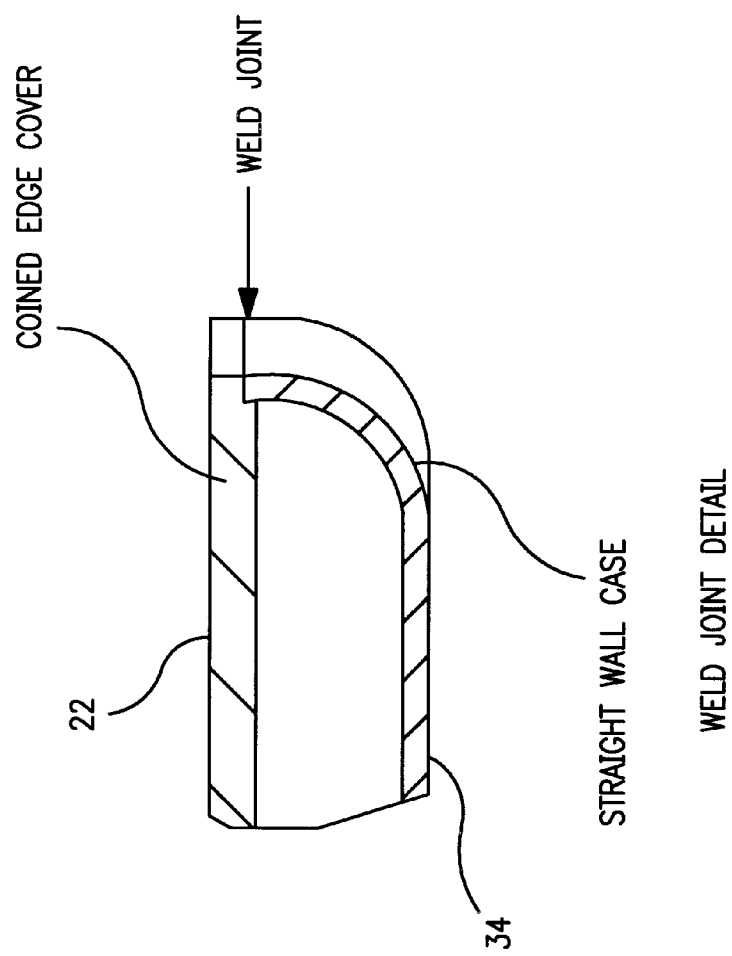
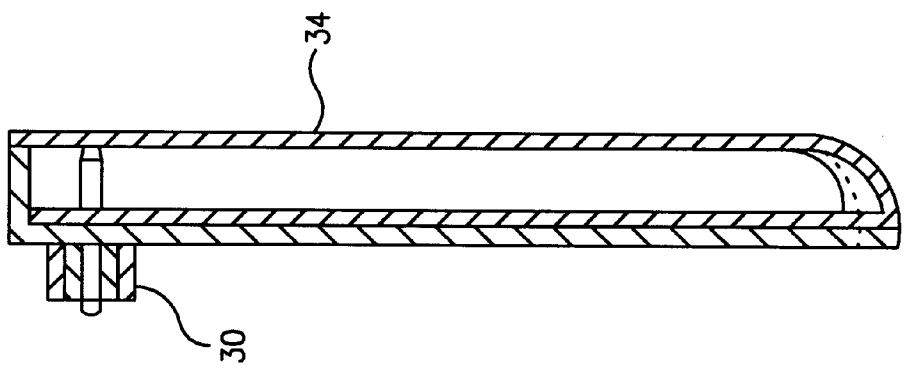

SECTION B-B

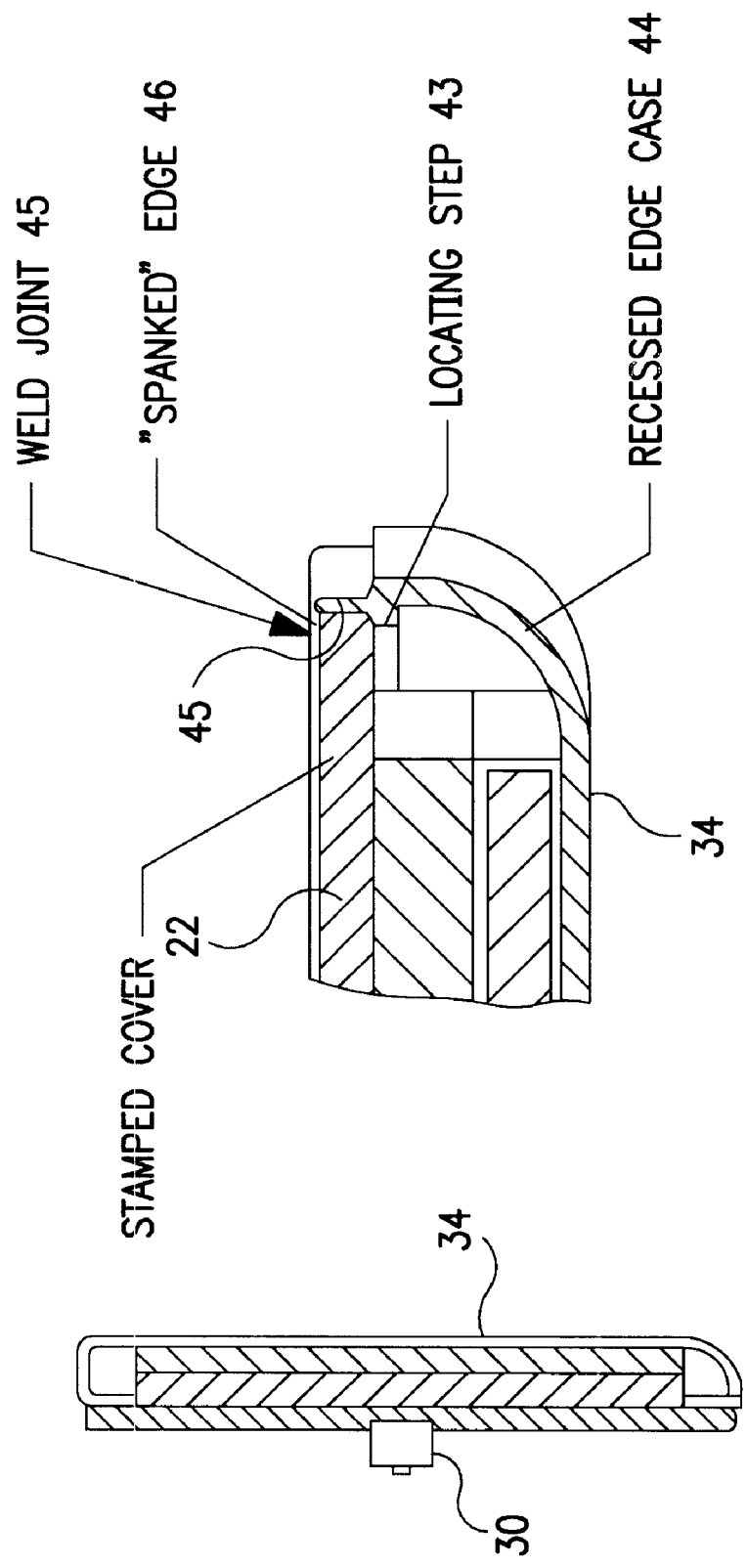

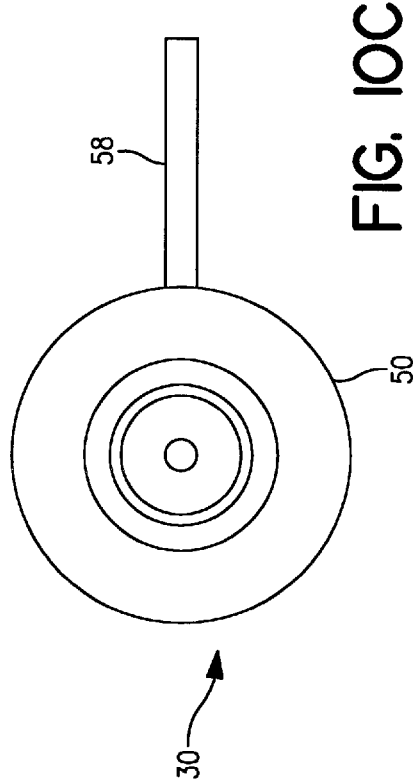
FIG. 10B
FIG. 10C
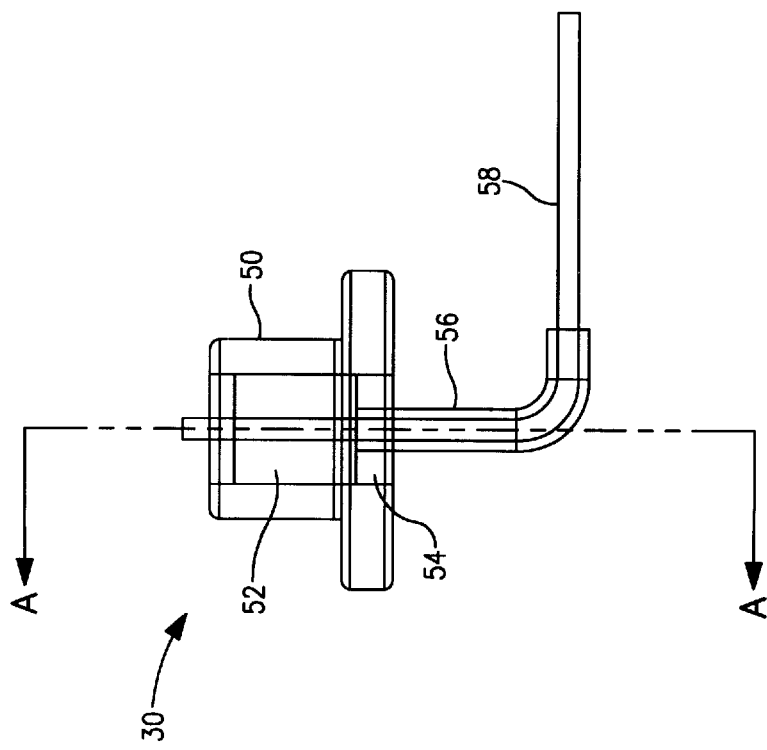
FIG. 10A

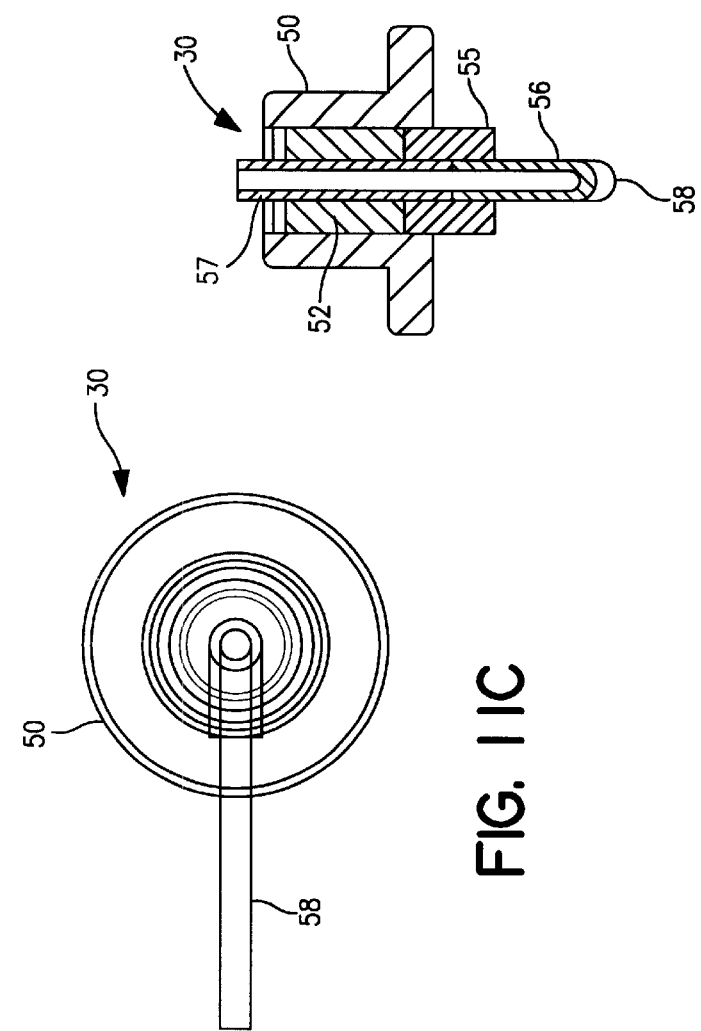
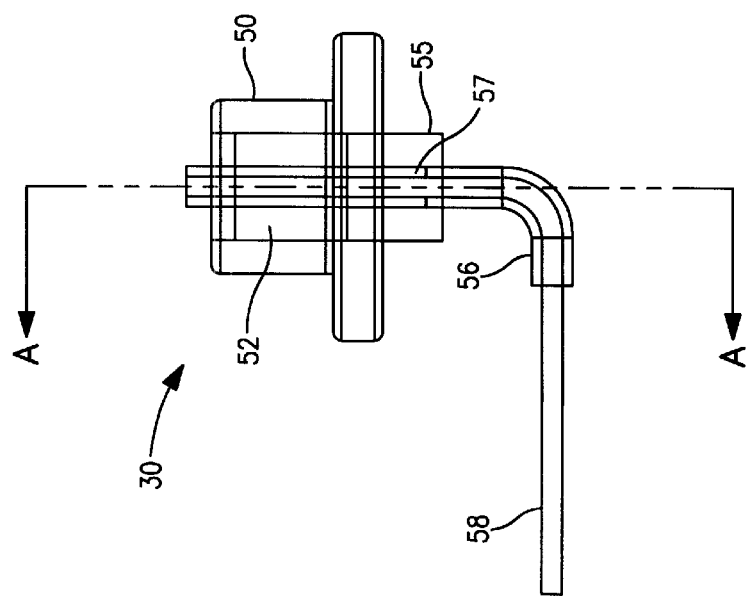
FIG. 11B
FIG. 11C
FIG. 11A

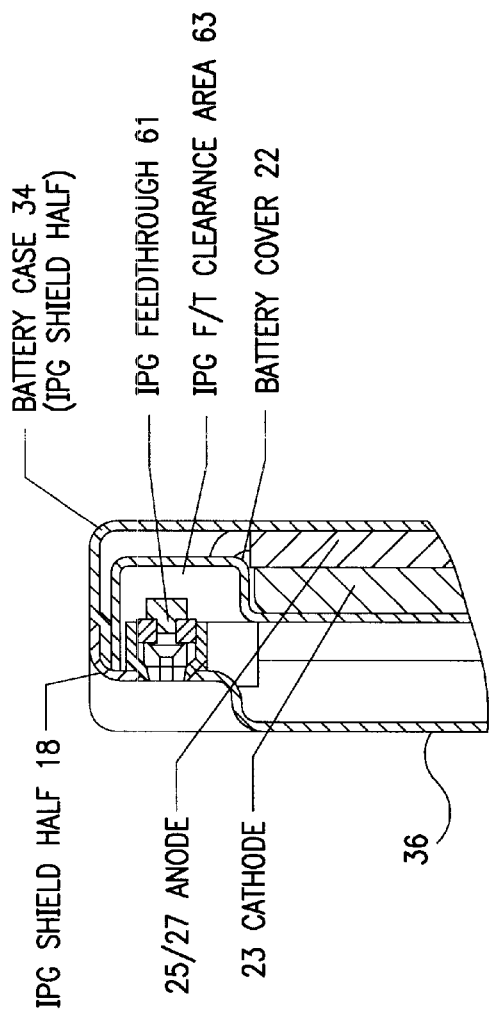
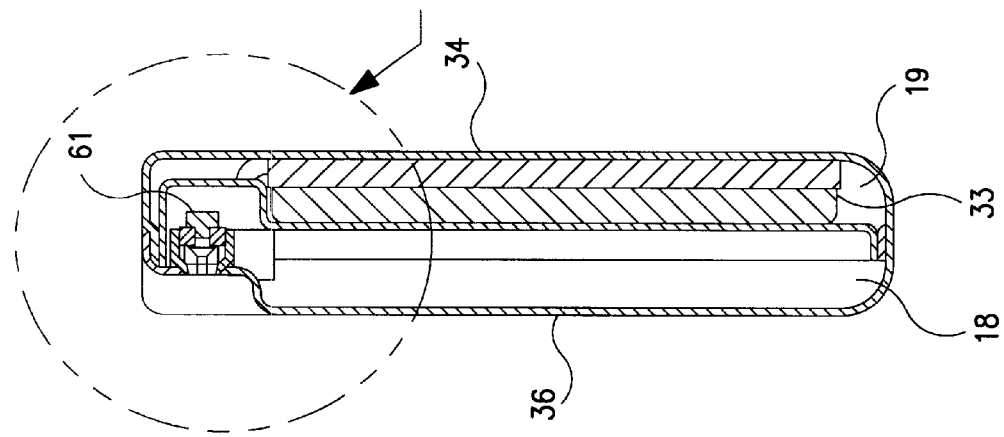

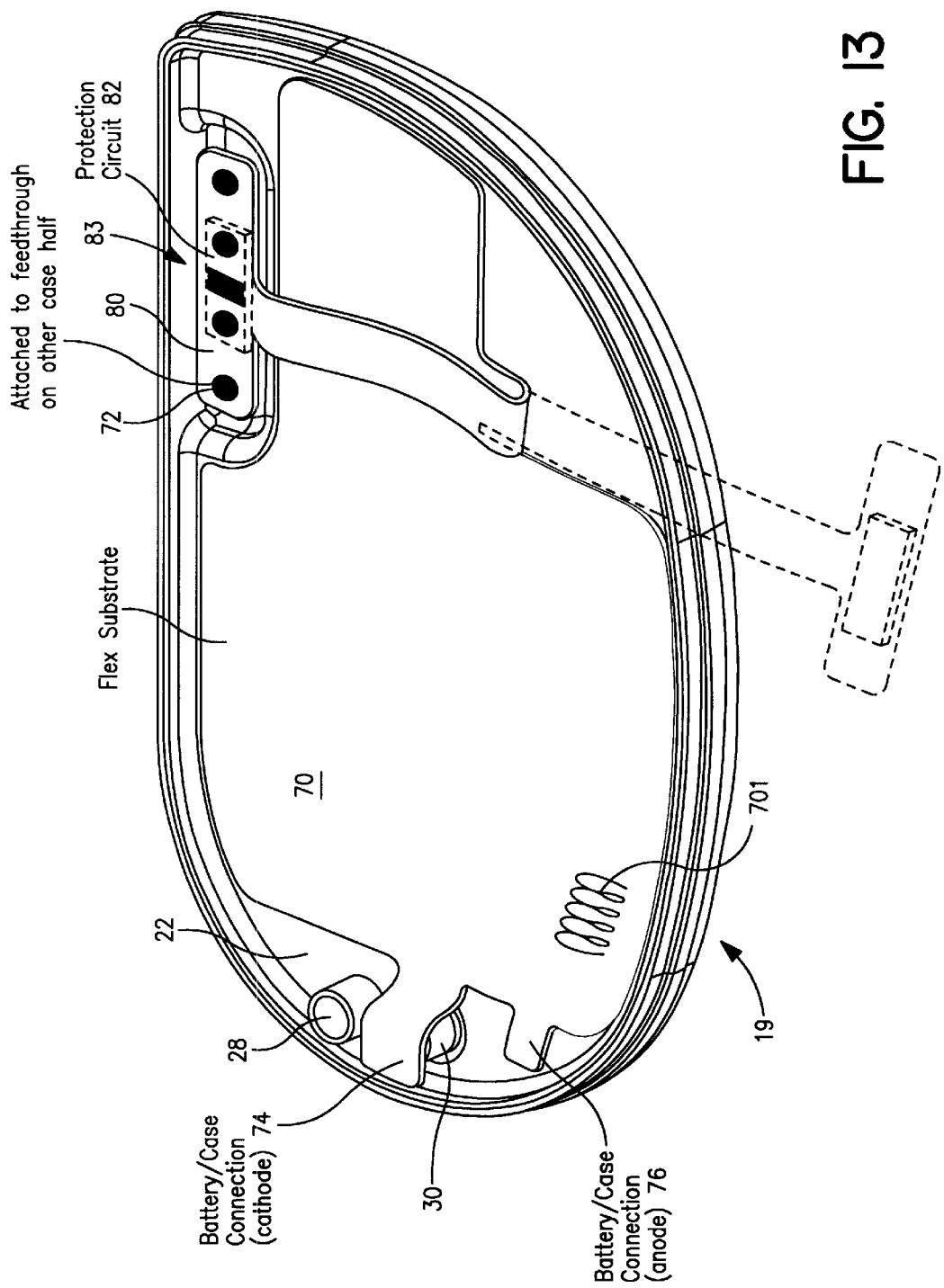

IMPLANTABLE MEDICAL DEVICE EMPLOYING INTEGRAL HOUSING FOR A FORMABLE FLAT BATTERY

FIELD OF THE INVENTION

The present invention relates generally to batteries for use with an implantable medical device (IMD). More particularly, the present invention pertains to an integral housing of an implantable medical device for containing a formable flat battery.

BACKGROUND OF THE INVENTION

As implantable medical device (IMD) technology advances in an attempt to address a myriad of life sustaining/enhancing needs, issues such as IMD battery longevity, IMD size and shape, IMD mass, and patient comfort remain key considerations in the IMD design process. Much attention is typically placed on the power source of an implantable medical device during the IMD design process. It is appreciated that battery size and capacity, for example, significantly impact the physical configuration of the IMD and the duration of service time within the patient before battery replacement is required.

A conventional approach to providing power within an implantable medical device involves the use of a self-contained battery, not unlike a common battery which is commercially available to the consumer. Such a self-contained battery includes active electrochemical cell components housed in a battery can. Battery housing connectors or contacts are provided for establishing electrical connections to circuitry disposed within in the implantable medical device.

It is well appreciated in the IMD manufacturing industry that the battery component of an IMD requires the allocation of an appreciable percentage of usable space within the IMD. It can be appreciated that reducing the size of the battery is a desirable design objective. However, reducing IMD battery size results in a corresponding reduction in battery capacity, which necessarily places limits on the ability to make significant battery size reductions using conventional IMD battery design principles.

Moreover, the can of a conventional IMD battery is often of a configuration that creates "dead space" within the implantable medical device (e.g., a can having a substantially square or rectangular shape). Although a thoughtful design approach can help to reduce the amount of such dead space, an appreciable volume of space within the IMD typically remains unusable when employing a conventional IMD battery. Also, the metal battery can that contains the active battery components must be of a thickness sufficient to protect against battery leakage. The thickness of the battery can must also be taken into consideration when allocating space within the IMD to house a battery source of a conventional design.

There is a need in the implantable medical device manufacturing community for an IMD battery implementation which provides for an overall reduction in IMD size without a corresponding reduction in battery capacity. There exists a further need for an IMD battery implementation that provides enhanced flexibility in terms of shape, size, and other form factor properties. The present invention fulfills these and other needs.

SUMMARY OF THE INVENTION

The present invention is directed to a selectable deformable housing assembly for an implantable medical device (IMD). An IMD housing according to the present invention includes a first shell and a second shell. The first and second shells include an inner surface and an outer surface, respectively. The outer surfaces of the first and second shells are fabricated from a material compatible with body fluids. The implantable medical device further includes a battery enclosure defined by a cover and all or a portion of the first shell of the IMD housing. The cover of the battery enclosure is disposed between the inner surfaces of the first and second shells and has a greater thickness dimension or higher modulus of elasticity than the first shell. An electrochemical battery cell, such as a flat liquid electrolyte battery, is provided in the battery enclosure. Electronic circuitry, supported on a flexible wiring substrate, which is electrically coupled to the electrochemical battery cell and a medical electrical lead, is provided between the inner surface of the second shell and the cover of the battery enclosure. A hermetic seal is provided between the cover of the battery enclosure and the applicable portion of the first shell.

The deformable housing assembly is further defined by a feedthrough assembly, which couples the battery to the electronic circuitry. The feedthrough assembly is disposed within a hermetically sealed aperture of the cover and includes a ferrule and a feedthrough pin that are isolated from one another.

The electrochemical battery cell is further defined to include a lithium anode, a cathode with Li/CSVO/CF$_x$ chemistry and a liquid electrolyte of type 1M LiBF$_y$ in GBL/DME.

The hermetic seal provided between the cover of the battery enclosure and the first shell is preferably a weld joint. In one embodiment, the battery enclosure cover includes a coined edge and the hermetic seal is established by a butt weld joint between the coined edge of the cover and a peripheral edge of the first shell.

According to another embodiment of the present invention, a housing assembly for an implantable medical device includes a housing comprising a first shell and a second shell, with the outer surfaces of the first and second shells including a material compatible with body fluids. The first shell includes a spanked edge. A battery enclosure is defined by a cover and at least a portion of the first shell of the IMD housing. The cover of the battery enclosure is situated between the inner surfaces of the first and second shells, has a greater thickness dimension or higher modulus of elasticity than the first shell, and includes a peripheral edge. A hermetic seal, according to this embodiment, is established by a spank weld joint between the peripheral edge of the cover and the spanked edge of the first shell.

The first shell may further include a first substantially straight peripheral wall portion and a second substantially straight peripheral wall portion adjacent to the first portion and offset from the first portion to form a ledge, which the peripheral edge of the cover engages. The hermetic seal is established by a spank weld joint between the peripheral edge of the cover and the spanked edge of the first shell.

According to yet another embodiment, the cover may also include a substantially straight peripheral wall portion. The hermetic seal is established by a standing edge weld joint between the substantially straight peripheral wall portion of the cover and the substantially straight peripheral wall portion of the first shell.

The present invention is also directed towards a method for assembling a battery into a housing assembly for an IMD including the following steps: providing a shallow drawn case; providing a battery cover having a greater thickness or higher modulus of elasticity than the case; coupling a cathode to the cover; glassing a feedthrough assembly having a feedthrough tube disposed within a ferrule to electrically isolate the feedthrough tube from the ferrule and to bond the feedthrough tube to the ferrule; hermetically sealing the ferrule of the feedthrough assembly to the cover; coupling a feedthrough pin to an anode current collector; placing an insulator tube over the feedthrough; placing the cover over the anode current collector while directing the feedthrough pin through the feedthrough tube; coupling the feedthrough pin to the feedthrough tube; and hermetically sealing the cover to the case.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 4 illustrates various elements of the flat battery and integral battery housing of FIG. 3;

FIGS. 5A–E are illustrations of a hermetically-sealed IMD battery housing according to another embodiment of the present invention;

FIGS. 6A–E illustrate another embodiment of a hermetically-sealed IMD battery housing of the present invention;

FIGS. 10A–D illustrate various showings of a feedthrough in accordance with one embodiment of the present invention;

FIGS. 11A–D illustrate another embodiment of a feedthrough according to the present invention;

FIGS. 12A–D illustrate various views of a complete implantable medical device employing a flat battery in accordance with an embodiment of the present invention;

FIG. 13 illustrates a flexible wiring substrate for supporting implantable medical device electronics in accordance with an embodiment of the present invention;

Figure 1:
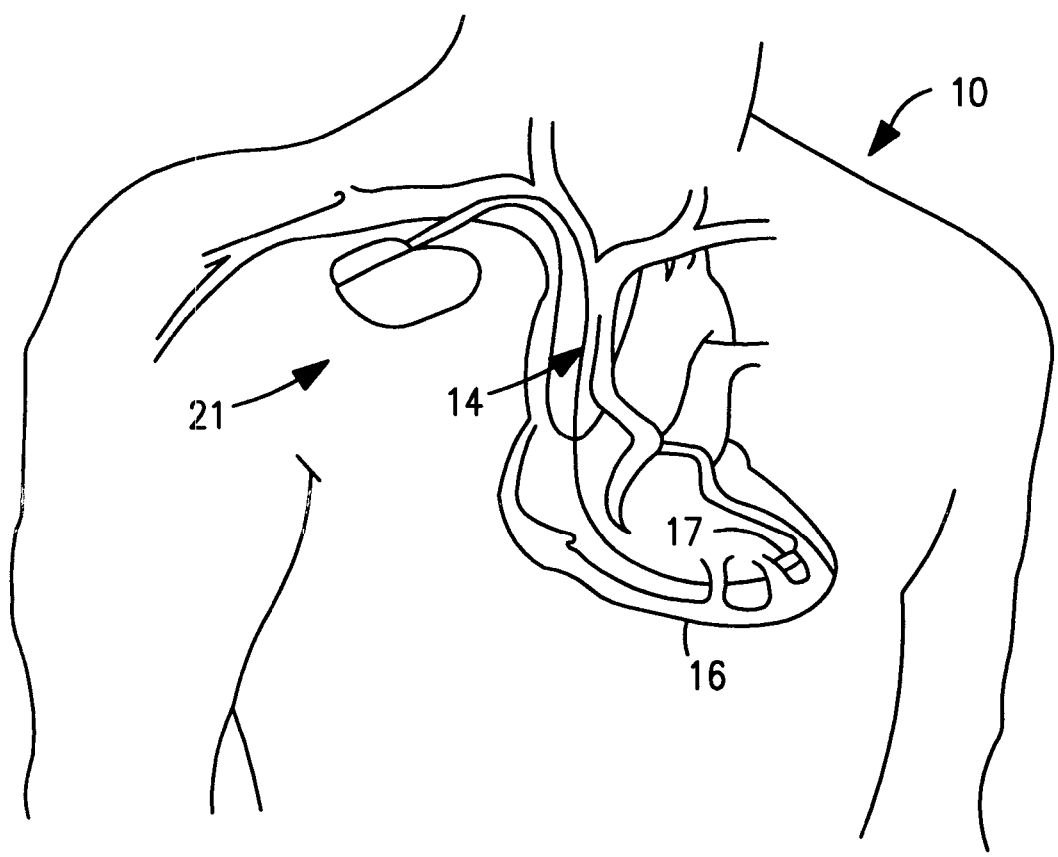
FIG. 1 is an illustration of an implantable medical device within a human body, the implantable medical device employing an integral battery housing for containing a flat battery and flexible wiring substrate according to the principles of the present invention.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

FIG. 1 is a simplified view of a medical device 21 implanted in a human body 10. The implantable medical device 21 shown in FIG. 1 employs a formable flat liquid electrolyte battery provided within an integral IMD battery housing in accordance with the principles of the present invention. According to one embodiment, IMD 21 incorporates a formable flat liquid electrolyte battery and a flexible wiring substrate that provides support for, and interconnection between, all or some of the electrical and electronic components of IMD 21.

FIG. 1 further shows a transducer assembly 17 implanted in a human heart 16 and coupled to IMD 21. The transducer assembly 17 includes a lead 14 to which one or more sensors are attached, each of which senses one or more physiologic parameters associated with the human heart 16.

In the case where the IMD 21 shown in FIG. 1 is a pacemaker, a conductor of lead 14 is typically connected between the heart 16 and IMD 21. The lead 14, which typically includes a tine electrode, senses electrical signals attendant to the depolarization and re-polarization of the heart 16 and transmits pacing pulses for causing depolarization of cardiac tissue in the vicinity of the distal ends thereof. The medical device 21 may be an implantable cardiac pacemaker, such as those disclosed in U.S. Pat. No. 5,158,078 to Bennett et al., U.S. Pat. No. 5,312,453 to Shelton et al., or U.S. Pat. No. 5,144,949 to Olson, hereby incorporated herein by reference in their respective entireties.

The implantable medical device 21 may also be a pacemaker/cardioverter/defibrillator (PCD), one embodiment of which is further described hereinbelow. The present invention may be practiced in conjunction with PCDs, such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties.

Alternatively, IMD 21 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as that disclosed in U.S. Pat. No. 5,331,966 issued to Bennet et al., all of which are hereby incorporated herein by reference in their respective entireties. The present invention is believed to find wide application in any form of implantable electrical device which utilizes a battery for providing power to various electrical and electronic components of the implantable medical device.

Figure 2:
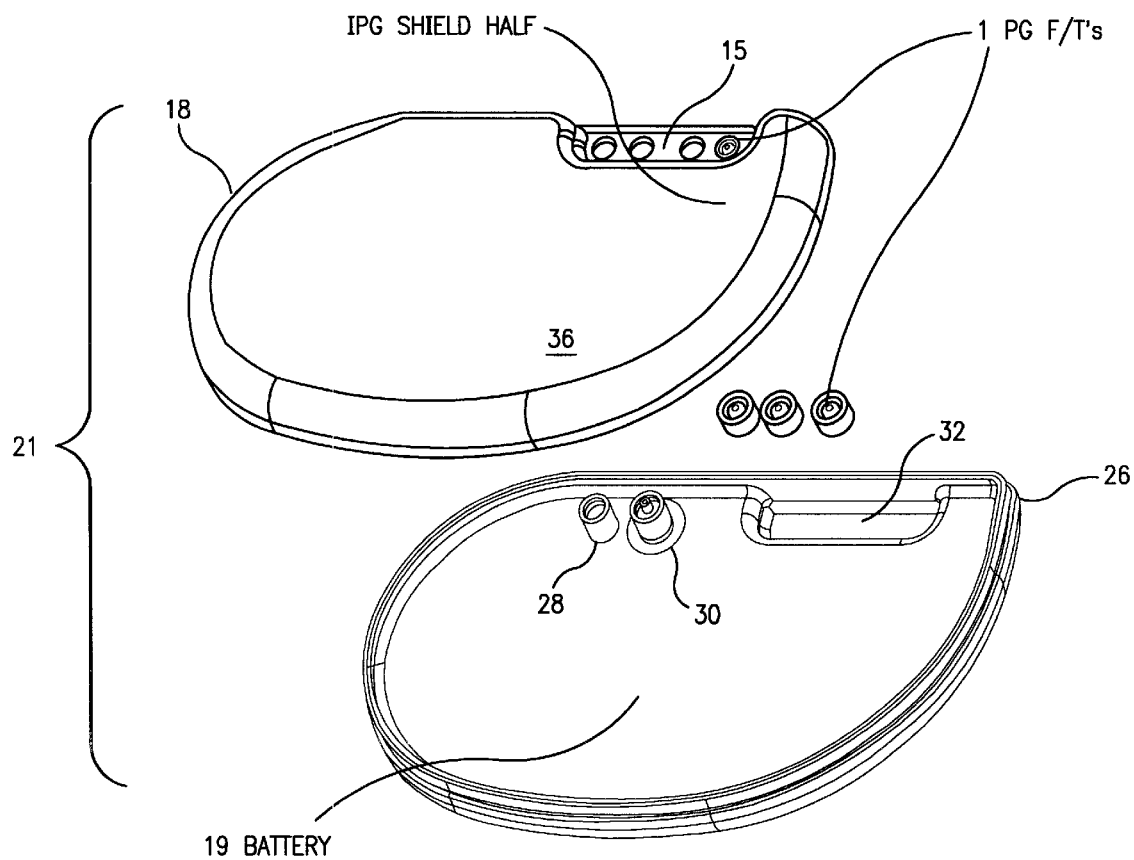
FIG. 2 illustrates two major sections of an implantable medical device employing a formable flat battery contained within an integral housing in accordance with an embodiment of the present invention.

FIG. 2 illustrates an implantable medical device 21, such as an implantable pulse generator (IPG), which incorporates an integral battery housing for containing a flat liquid electrolyte battery in accordance with the principles of the present invention. The implantable medical device 21 shown in FIG. 2 includes two major sections, namely, an IMD shield section 18 and an IMD battery section 19. A flexible wiring substrate (not shown in FIG. 2) of the present invention is typically disposed between the IMD shield and battery sections 18, 19.

The IMD shield section 18 is shown to include a recessed region 15 for accommodating a number of implantable medical device feedthroughs. The IMD feedthroughs represent hermetically-sealed connector assemblies which provide for electrical connectivity between a pacing or sensing lead, for example, and IMD electronics disposed within the protective housing 18, 19 of IMD 21.

Battery section 19 includes a corresponding recessed region 32 for accommodating the IMD feedthroughs. Battery section 19 further includes at least one battery feedthrough 30 and a fillport 28. Battery section 19 incorporates a thin, flat liquid electrolyte battery provided within a hermetically-sealed battery housing 26.

Figure 3:
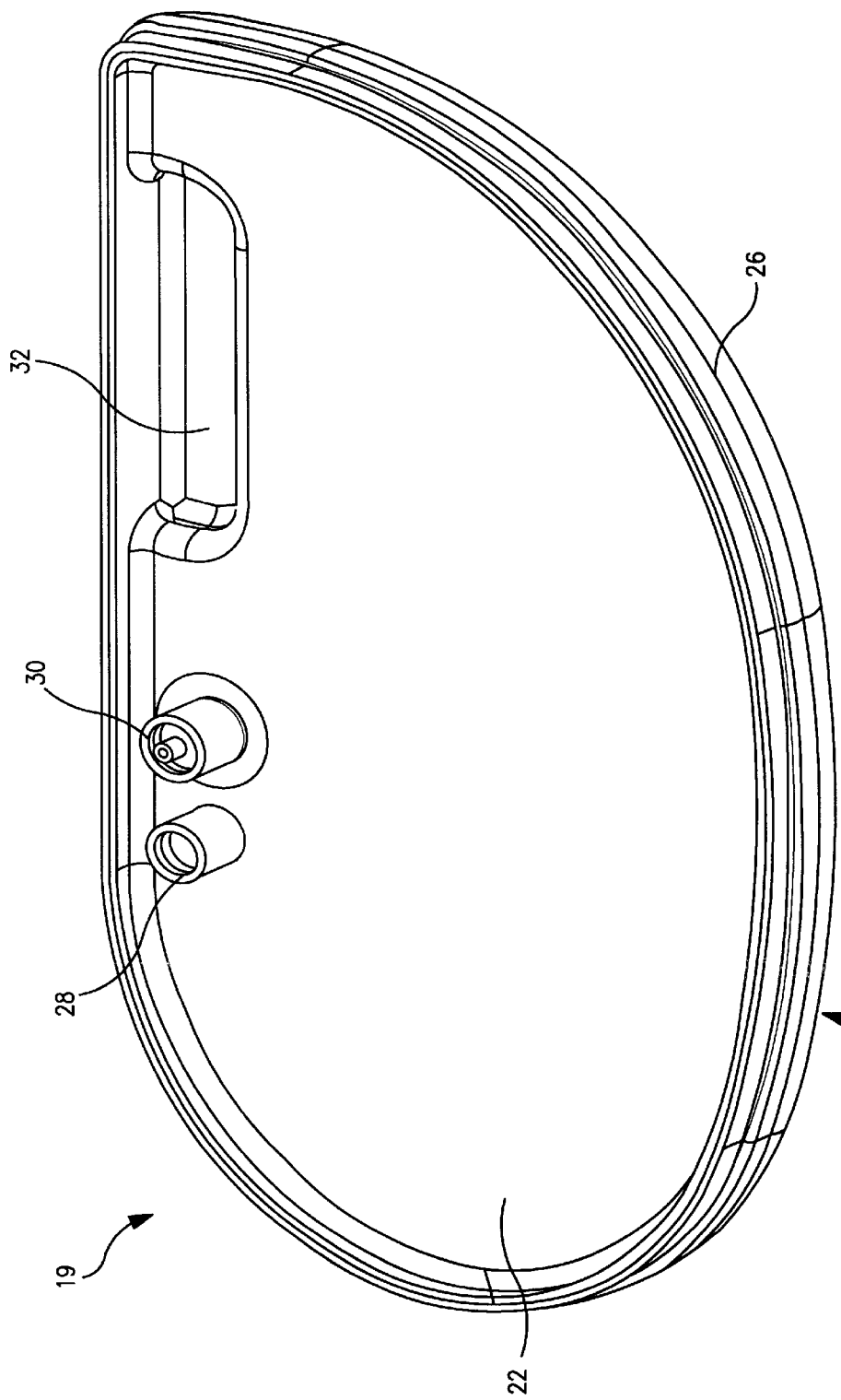
FIG. 3 illustrates an integral battery enclosure of an implantable medical device according to an embodiment of the present invention.

In accordance with the principles of the present invention, and as shown in FIG. 3, IMD 21 employs a shallow-drawn hermetically-sealed case 26 which houses the active elements of a flat liquid electrolyte battery. Implantable medical device 21 is shown to include a fillport 28 and a battery feedthrough assembly 30, each of which passes through the cover 22 of the implantable medical device 21. Battery feedthrough assembly 30 and fillport 28 each include a hermetic seal between the apertures provided in cover 22 and the respective assembly 30 and fillport 28. An IMD feedthrough region 32 is provided within a recessed portion of the cover 22.

A significant advantage realized through employment of an implantable medical device 21 which incorporates a shallow-drawn case 26 of the present invention concerns the manner in which naturally occurring swelling of the flat liquid electrolyte battery is managed within the battery housing 26. More particularly, employment of a shallow-drawn case 26 and thoughtful layout of internal IMD components provides for swelling of the flat liquid electrolyte battery which is biased in a direction away from the electronics. Moreover, an enhanced degree of shape flexibility or formability is achievable, thus permitting the battery to fit the contour of the IMD housing.

The term shallow-drawn case is intended to represent a housing or case in which the draw direction of the case is the smallest of the three overall dimensions. The shape of the largest face, which is best seen in FIG. 3, includes both curved and straight sections. In the embodiment shown in FIG. 3, for example, the curved sections represent a significant portion of the perimeter of the case 26.

According to the present invention, the case 26 may include complex curved portions, such as scalloped portions, in addition to or to the exclusion of straight sections. For example, the case 26 may be formed to have a shape considered non-standard within the implantable medical device industry.

By way of further example, case 26 may be designed to follow the contour of a D-shaped battery or, alternatively, may be configured to have a largely prismatic shape with one corner radiused more generously than others. Employment of a thin flat cell in conjunction with thoughtful electronics packaging provides for complex battery and IMD housing shapes. In general, providing an IMD housing which is more rounded increases patient comfort and diminishes the risks of lead damage, tissue erosion, and infection by eliminating sharp device corners. A formable battery and formable flexible wiring substrate implemented in accordance with the principles of the present invention advantageously provides for optimization of the available IMD housing space, as the battery and wiring substrate may be formed to closely track the contour of the IMD housing.

According to this embodiment of battery housing 26, the cover 22 extends down into the shield half of the implantable medical device to provide more clearance for the implantable medical device components. A clearance area 32 is stamped into the cover 22 to allow clearance for the implantable medical device feedthroughs.

An important aspect of the implantable medical device 21 depicted in FIGS. 3 and 4 concerns the dual use of cover 22 as both an exterior shield of the implantable medical device and a wall of the internal battery housing. In the embodiment depicted in FIG. 4, for example, cover 22 represents approximately one-half of the IMD housing, as well as approximately one-half of the battery housing. Accordingly, the battery housing defines an appreciable portion of the implantable medical device exterior which is exposed to body fluid. The IMD electronics, which are preferably supported on, and interconnected using, a flexible wiring substrate, are disposed between the cover 22 of the battery and the other half or portion of the IMD shield.

In the embodiments depicted in FIGS. 3 and 4, the cover 22 of the cell 33 defines one of the large faces of the shallow-drawn case 26 and is either the same material thickness as the case 34 or of a thicker material. Since cell swelling during charge and discharge cycling is a characteristic of some of the battery chemistries that could be used within the battery housing 26, a thicker cover 22 generally provides for increased rigidity on one side of the battery 33. Increasing the rigidity of a specific side of the battery 33 encourages swelling of the cell 33 in a given direction. The cover 22 can be constructed from the same material as the case 34 or a different material to facilitate weldability of the cover 22 with the case 34.

An implantable medical device which employs a dual purpose cover 22 of the type depicted in FIGS. 3 and 4 allows for more effective utilization of available IMD volume for battery packaging. Since the battery conforms to the shape of the implantable medical device, "dead space" within the implantable medical device can instead be used for the battery. As such, higher capacity batteries may be developed for a wide range of implantable medical devices without having to increase the device volume.

For example, it has been found that an implantable medical device constructed accordance with the principles of the present invention may provide for an increase of 10% to 13% in battery capacity over a conventional implantable medical device of equivalent size. In addition to increased battery capacity, battery mass may be reduced by roughly 50% in comparison to a conventional IMD battery of equivalent capacity.

Such capacity gains and mass reductions are achieved by eliminating an appreciable portion of the battery housing (e.g., battery case portion that would otherwise be situated adjacent an IMD shield), and by using freed-up space in the IMD shield half that would otherwise be occupied by parts such as an insulator cup, which can be wholly eliminated. This freed-up "dead space" volume may now be used for active battery components. As such, increased IMD service life may be realized without increases in device volume. Alternatively, the freed-up dead space can be allocated for additional leads, additional electronics or the implantable medical device size could be reduced.

A number of additional advantages may be realized through employment of a shallow-drawn IMD housing of the present invention. One important advantage, as discussed above, concerns the ability to bias cell swelling to one direction, such as by making the battery housing cover 22 thicker, constructing the cover 22 using a material of higher modulus relative to the case 34, or the combination of using a thicker, higher modulus cover material relative to the case material.

The ability to produce IMD batteries or cells 33 which are very thin, such as less than 0.135 inches, is also realizable. It is noted that the limit for a conventional deep-drawn IMD battery housing is approaching 0.240 inches. In contrast to a conventional housing implementation, a shallow-drawn IMD housing of the present invention provides for a battery form factor of significantly reduced size (e.g., nearly one-half that of a conventional battery housing). Further, a battery housing of the present invention can be made to fit the contour of the IMD can as desired, which represents a level of formability not achievable using conventional battery implementations.

Employment of a shallow-drawn IMD housing according to the present invention also provides for easier implantable medical device assembly. For example, straight-down assembly techniques may be employed, which significantly reduces the risk of damaging components upon insertion of same into the housing. Moreover, a straight-down assembly process may be easily adapted to automation, thereby enhancing the efficiently and cost of assembling implantable medical devices.

Another advantage concerns enhanced feedthrough orientation flexibility. The feedthrough assembly for establishing connectivity with the cell 33 may be made normal to either the cover 22 or the case 34. The bulk of the feedthrough assembly 30 (e.g., ferrule/glass interface) may be either inside or outside of the battery housing 26. The feedthrough assembly 30 can also protrude from a shelf formed within the case 34. Orienting the feedthrough pin of the assembly 30 to be perpendicular to the cover 22 when the battery 33 is packaged provides for easy attachment of the feedthrough pin to the opposing electronics module, preferably provided on a flexible wiring substrate. Other advantages include reduced implantable medical device housing costs (e.g., fewer draws and anneals), simplified cover configuration, ease of fabrication, and handling. Such a housing is also easier to clean, thus reducing the chance of metal particles being introduced into the cell 33.

With continued reference to FIG. 4, the cell construction and chemistry according to one embodiment of the present invention will now be described. FIG. 4 illustrates one embodiment of a thin, flat liquid electrolyte battery well suited for use within a shallow-drawn case of the type described with reference to FIG. 3. The battery shown in FIG. 4 includes a cathode pellet 23, an anode assembly 27, and an anode current collector 25 disposed therebetween. The chemistry of the battery of cell 33 typically employs a liquid electrolyte, such as 1N Li $AsF_6$ in PC/DME with Li/CSVO chemistry. It is understood that the chemistry of a particular IMD cell may require liquid electrolytes of differing formulation. For example, suitable liquid electrolyte chemistries may include $Li/MnO_2$, Li/SVO, $Li/CF_x$ and $Li/SVO$—$CF_x$.

According to one embodiment, the anode assembly 27 includes a lithium anode, and the cathode pellet 23 includes a hybrid cathode chemistry described by an $Li/CSVO/CF_x$ chemistry. The liquid electrolyte has a chemistry described by 1M $LiBF_y$ in GBL/DME. The hybrid cathode chemistry according to this embodiment offers several advantages over other available medium rate chemistries. The shallow-drawn IMD battery 33 has roughly one-half the $Li/I_2$ battery mass as compared to a conventional deep-drawn IMD battery of equivalent capacity. Moreover, the shallow-drawn IMD battery 33 exhibits energy densities which are comparable to conventional $Li/I_2$ IMD batteries at low rates, and are significantly higher at increased discharge rates. A hybrid cathode chemistry of the present invention typically exhibits an increase in energy density of about 15% as compared to a conventional Li/CSVO chemistry. Further, such a hybrid cathode chemistry provides for a relatively low degree of cell swelling.

It is desirable that the flat cell 33 leverage existing fabrication technologies from high rate and medium rate mechanical platforms. A high cathode fabrication technology, for example, may be used to fabricate the cathode 23. One large, flat cathode 23 may be fabricated using either an expanded metal screen or a perforated, etched screen as a cathode current collector.

The cathode current collector may be fabricated with tabs to facilitate attachment of the cathode to the cover 22. The cathode is preferably welded to the cover 22 to maximize the distance between the anode 27 and the case-cover weld joint. Since a polyolefin film laminate is preferably used as an electrode separator, maximizing the distance from the heat affected zone is an important design consideration. The anode 27 is preferably double-bagged in a polyolefin film laminate to provide two layers of protection between electrodes and between the anode and the case.

The anode 27 uses an etched current collector. A nickel anode current collector may also be used to improve anode processing by eliminating anode brushing during pressing. Medium rate assembly technology may be used to fabricate the anode 27.

The case 34 and cover 22, according to this embodiment, are fabricated from surgical Grade I titanium. Since the battery enclosure is subjected to body fluid, surgical Grade I titanium is preferred. Grade I titanium is also preferred for stamped part fabrication. The case 34 may have a nominal material thickness between 0.012 and 0.015 inches. The cover 22 may have a nominal material thickness of 0.030 inches.

The feedthrough assembly 30 includes a ferrule which is constructed from Grade III titanium. Grade III titanium is preferred for machine part fabrication. The fillport seal may be implemented using a variety of known approaches. The feedthrough glass may be constructed from CABAL-12 or other polymer. The feedthrough pin 34 may be fabricated from titanium or niobium with glass. Alternatively, a nickel pin with polymer feedthrough may be employed. Titanium or niobium pins with tubes may also be employed as an alternative. It is understood that the feedthrough assembly 30 may be positioned at different locations on the cover 22 and may be configured to accommodate differently-shaped electrodes. The feedthrough assembly 30, however, should be located so as not to impinge on the region 32 dedicated for IMD lead feedthroughs.

The cell separator and absorbent layers may include polyolefin film laminate. The insulators may be propylene or propylene with alumina. The cathode pellet 23 may include a cathode having an embedded cathode current collector which leverages high rate cathode manufacturing processes. The cathode current collector may have tabs which are welded to the cover 22. The anode assembly 27 may be fabricated using a medium rate process with a current collector pressed onto the back of the anode. The anode current collector may be welded to the feedthrough pin 35 of the feedthrough assembly 30. The separator may be established using a standard heating/sealing process or an ultrasonic sealing process.

Figure 5A:
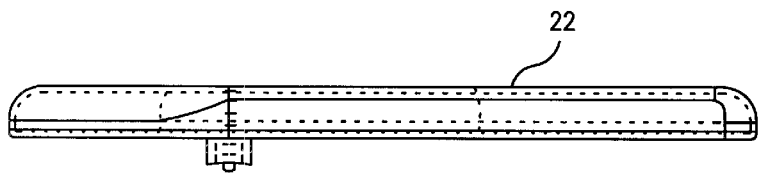
Figure 5B:
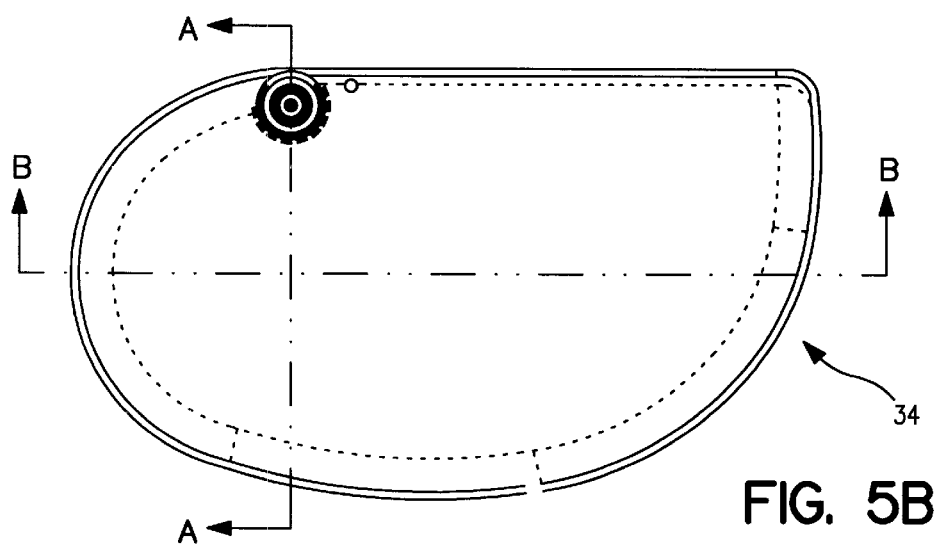
Figure 5C:
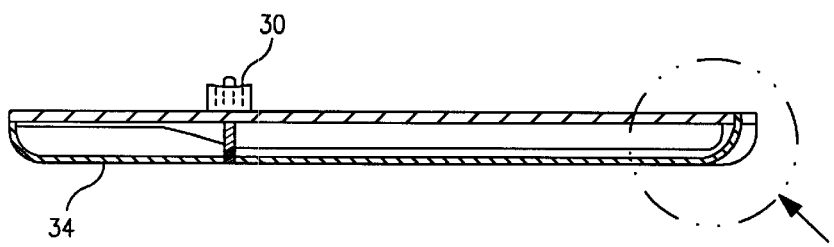

FIGS. 5–9 depict several different weld joints which may be used to hermetically seal the battery housing cover 22 and case 34 of an implantable medical device. FIG. 5 shows an embodiment of an implantable medical device employing a flat liquid electrolyte battery in which the IMD housing is hermetically-sealed using a butt seam weld joint. FIG. 5A shows a cover 22 of the implantable medical device, while FIG. 5B is a top view of the implantable medical device case 34. FIG. 5C is a showing of FIG. 5B taken through cross-section B—B, and FIG. 5D is a showing of FIG. 5B taken through cross-section A—A. FIG. 5E is an exploded view of the butt seam weld joint indicated by the dashed circle of FIG. 5C. The butt seam weld joint of FIG. 5E is depicted in a more simplified form in FIG. 7.

Figure 7:
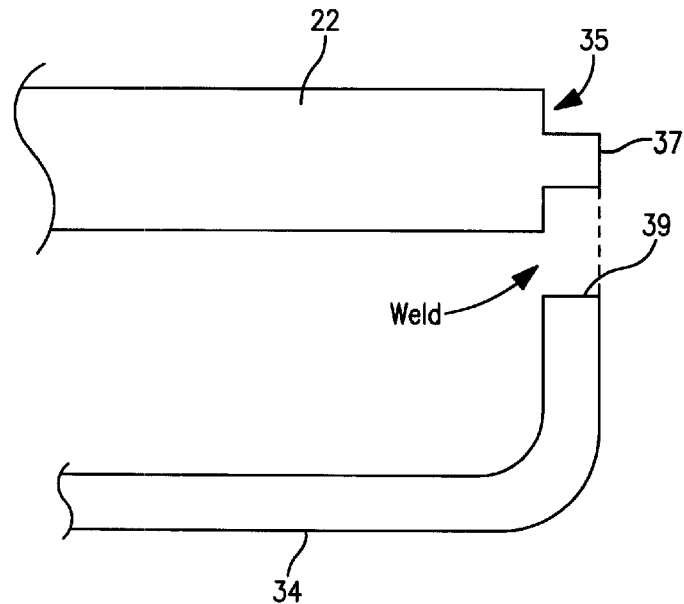
FIGS. 7–9 illustrate various embodiments of weld joints for hermetically sealing an IMD battery housing of the present invention.

With particular reference to FIGS. 5E and 7, the cover 22 of the battery housing 26 includes a peripheral coined edge 35. The coined edge 35 includes a coined portion 37 which registers with a contact step 39 of the straight wall case 34. With the coined portion 37 resting on the contact step 39, a butt seam joint is formed using a conventional welding technique, such as a tumble weld technique.

Figure 6A:
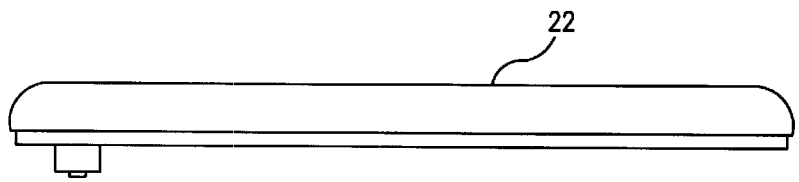
Figure 6B:
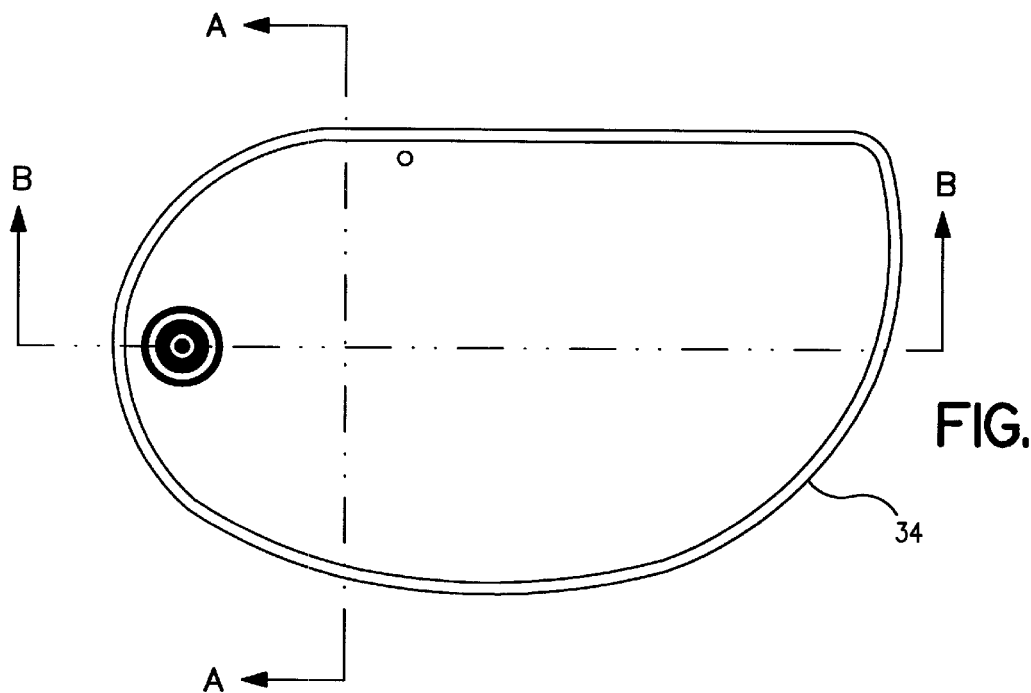
Figure 6C:
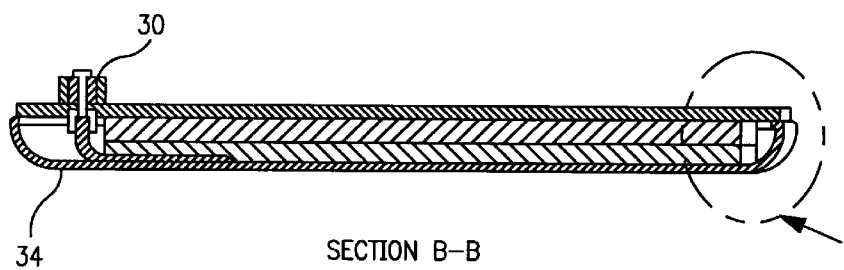
Figure 8:
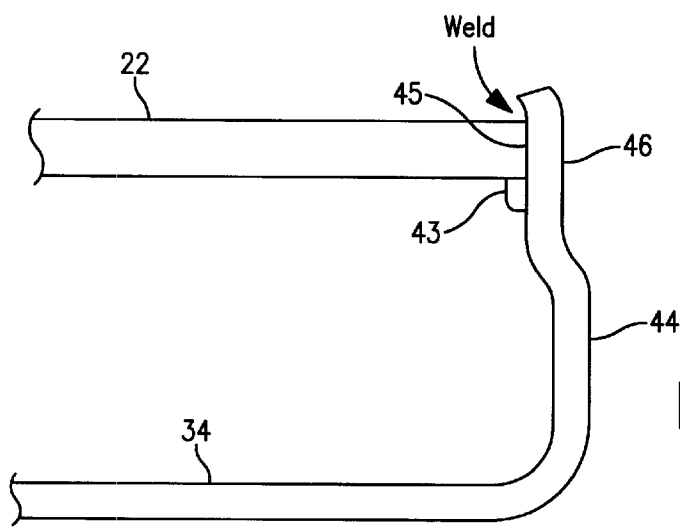

FIGS. 6 and 8 illustrate another battery housing configuration in which a spanked weld joint is formed to hermetically seal the IMD battery housing 26. FIG. 6A is a showing of the battery housing cover 22, and FIG. 6B is a top view showing of the case 34. FIGS. 6C and 6D are cross-sectional views of FIG. 6B taken through sections B—B and A—A, respectively. FIG. 6E is an exploded view of the spanked weld joint indicated by the dashed circle of FIG. 6C.

With reference to FIGS. 6E and 8, case 34 is shown to include an offset edge portion 44, a locating step 43, and a spanked edge 46. The cover 22, which according to this embodiment is a stamped cover, includes a peripheral edge 45 which, when registered on locating step 43 of case 34, abuts spanked edge 46 of case 34. A spanked weld joint 45 is then formed using a known welding technique.

Figure 9:
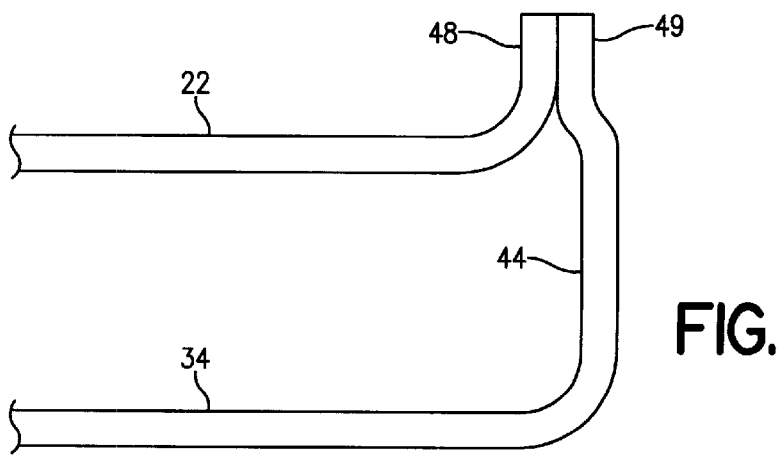

FIG. 9 illustrates yet another weld joint embodiment for hermetically sealing an IMD battery housing in accordance with the principles of the present invention. According to this embodiment, cover 22 represents a formed cover which includes a standing edge 48. The case 34 includes an offset portion 44 and a standing edge 49. A standing edge weld joint is then formed at an interface of the standing edges 48 and 49 using a conventional technique.

In FIGS. 5–9, the cover 22 may be fabricated to have a thickness of 0.030 inches. The case 34 may have a thickness of between 0.012 and 0.015 inches. It is understood that the thickness of the cover 22 and case 34 may be varied according to the materials employed and configuration of the implantable medical device and battery housings. The thickness and material of the cover 22 and case 34 may be further varied to facilitate selective control of the swelling direction of the flat liquid electrolyte battery housed between the cover 22 and case 34.

FIG. 10 is an illustration of a battery feedthrough assembly 30 in accordance with one embodiment of the present invention. Those skilled in the art will appreciate that the rather large, planer electrodes of a thin, flat liquid electrolyte battery of the present invention (see FIG. 4) complicates electrode attachment and feedthrough insulation considerations. The electrodes shown in FIG. 4, for example, are rather large, thin kidney-shaped electrodes. During assembly, the anode of the battery 33, for example, is pressed with just the feedthrough 30 welded to the anode current collector 25. The anode is then attached to the battery 33 by welding the feedthrough 30 into the cover 22 after the anode has been pressed and the separator sealed.

Figure 10D:
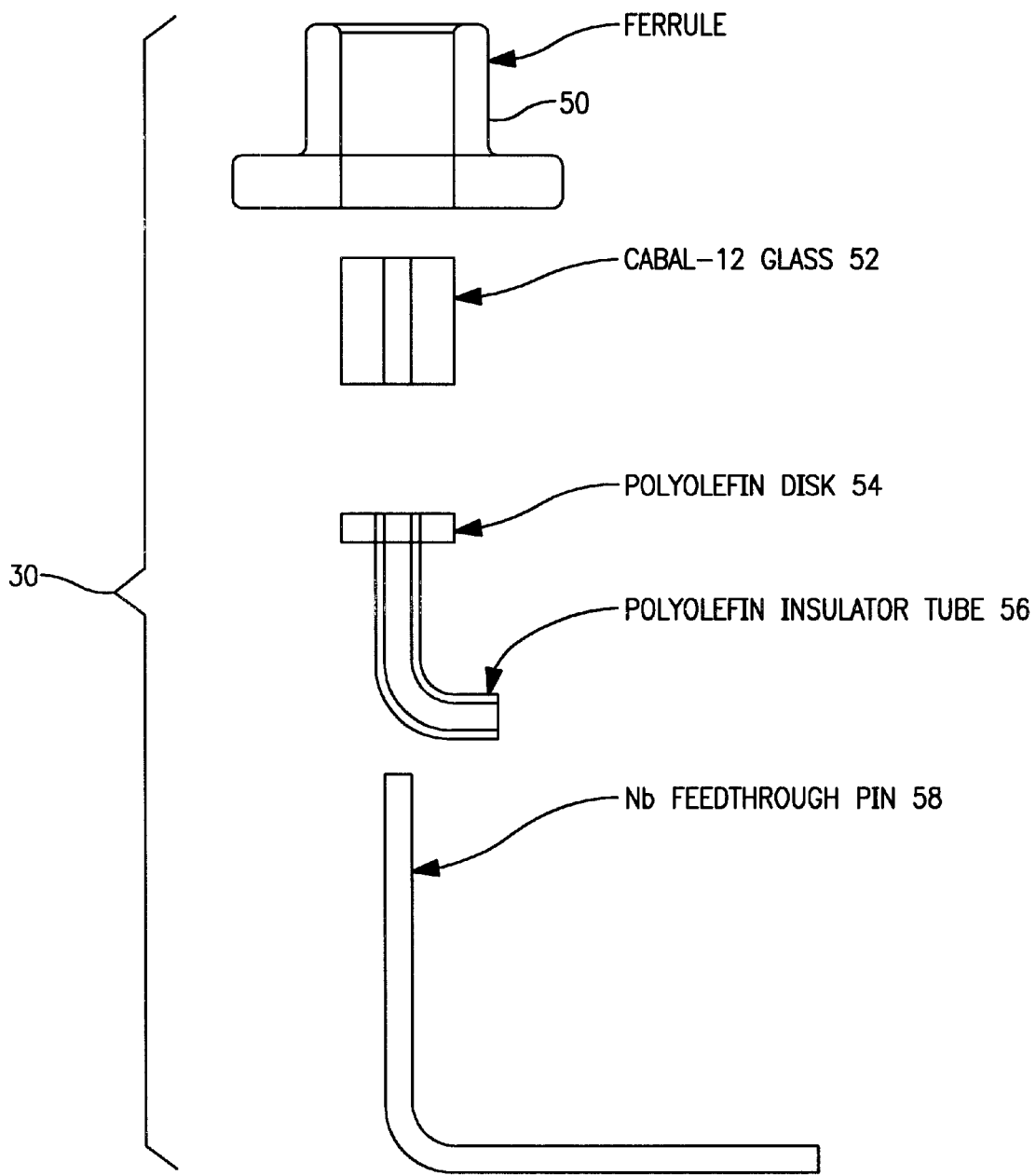

FIG. 10A is a side view of feedthrough 30 according to this embodiment. FIG. 10B is a cross-sectional view of the feedthrough 30 shown in FIG. 10A taken along section A—A. FIG. 10C is a top view of feedthrough 30 shown in FIG. 10A, and FIG. 10D is an exploded view of various components of feedthrough 30 shown in FIG. 10A.

As best seen in FIG. 10D, feedthrough 30 includes a niobium (Nb) feedthrough pin 58 which passes through an insulator tube 56, such as a tube constructed from polyolefin. The feedthrough pin insulator further includes an insulating disk 54 which may also be fabricated from polyolefin.

The insulator tube 56 is "glassed" with a sealing glass, such as a CABAL-12 glass member 52. The insulating disk 54 and insulator tube 56 are press fit into the ferrule 50 to form a compression seal. This arrangement provides the necessary electrical and physical insulation between the feedthrough pin 58 and regions of opposite polarity. During assembly, the anode of the battery 33 is typically fabricated with the feedthrough 30 in place. When the battery 33 is assembled, the feedthrough 30 is welded into the cover 22 so as to secure the anode to cover assembly.

Due to the size of the cover 22, glassing the feedthrough 30 using conventional methods may not be efficient. It may, therefore, be desirable that the feedthrough 30 be glassed in the ferrule 50 as a discrete part and then welded into the cover 22. The feedthrough 30 may be assembled to include an MP-35N ferrule 50 and TA-23 glass. It is noted that the insulating disk 54 and insulator tube 56 arrangement provides for electrical insulation and protection against lithium ball formation. An ETFE coating may be applied to the feedthrough 32 to ensure protection from the lithium ball formation.

Figure 11D:
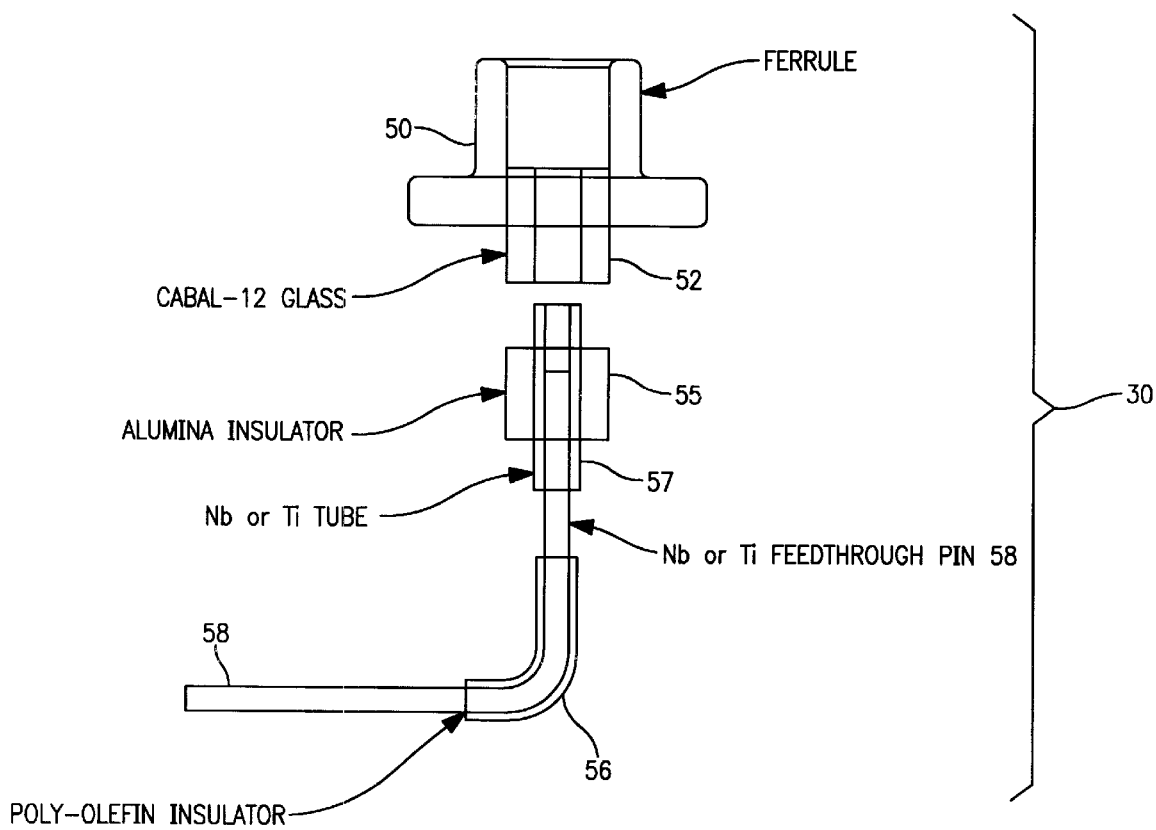

FIG. 11 illustrates another embodiment of a feedthrough assembly according to the present invention. FIG. 11A is a side view of feedthrough 30 according to this embodiment. FIG. 11B is a cross-sectional view of the feedthrough assembly 30 shown in FIG. 11A taken along section A—A. FIG. 11C is a top view of feedthrough 30 shown in FIG. 11A, while FIG. 11D is an assembly view of feedthrough 30 shown in FIG. 11A. According to this feedthrough embodiment, the anode is attached to the feedthrough assembly 30 by passing feedthrough pin 58 through a tube 57 and welding the pin 58 in the end of the tube 57. The pin 58 is then welded to the anode current collector, such as collector 25 shown in FIG. 4. The tube 57 and feedthrough pin 58 may be constructed from Nb or titanium.

An insulator tube 56, such as one constructed from polyolefin, is slipped over the feedthrough pin 58, and one end of the insulator tube 56 is embedded in the feedthrough pin 58 when lithium is pressed to the anode current collector 25. The feedthrough 30 shown in FIG. 11 further incorporates an insulator cylinder 55, such as a ceramic cylinder, preferably an alumina cylinder, provided around the tube 57. The alumina insulator 55 shown in FIG. 11 may be obtained as a commercially-available part. Alternatively, a custom-shaped part may be employed to effectively seal the end of the feedthrough and provide an anchoring point for the polyolefin insulator tube 56. Insulator cylinder 55 bonds to the glass 52 and the tube 57, thus eliminating any shorting path between the tube 57 and the ferrule 50.

The feedthrough pin 58 in the anode is bent and the insulative tube assembly is slid up inside the insulator cylinder 55 and seated against the bottom of the feedthrough cylinder to complete insulation of the feedthrough assembly 30. The feedthrough pin 58 may be later welded to the end of the tube 57 to complete the battery assembly process. The feedthrough pin 58 is also welded to the cover 22 of the battery housing. The feedthrough assembly 30 is also welded to the cover 22 of the battery housing. This provides for "line of sight" isolation of the feedthrough pin 58 and the feedthrough ferrule 50 to prevent lithium ball shorting. It also provides an easy method for attaching the anode to the feedthrough assembly 30.

The feedthrough embodiment illustrated in FIG. 11 provides several advantages over conventional feedthrough fabrication processes. For example, the alumina insulator 55 bonds to the glass 52 and to the tube 56, thus creating a line of sight insulation between the feedthrough tube 57 and the ferrule 50. By covering the end of the feedthrough pin 58 with the polyolefin insulator tube 56 and inserting it into the alumina insulator 55, the feedthrough pin 58 is completely insulated, thereby eliminating the need to perform an ETFE or other insulative coating process. Elimination of the ETFE coating process reduces production scrap and simplifies the feedthrough assembly process.

In such an embodiment, the anode is pressed with a feedthrough pin 58 welded to the anode, rather than a complete feedthrough assembly 30. This configuration eliminates potential damage to the feedthrough 30 during the anode pressing process. Since the feedthrough 30 is welded to the cover 22, the feedthrough pin 58 can be welded to the tube 57 during the same welding process. The cost of welding the feedthrough pin 58 to the feedthrough tube 57 should be negligible.

A third feedthrough embodiment may include a polymer feedthrough using a nickel feedthrough pin. It is noted, however, that nickel cannot be used with CABAL-12 glass due to a severe thermal expansion mismatch therebetween. A molded part incorporating an insulative tube can be fabricated which effectively protects the feedthrough pin.

It is noted that an alumina or other ceramic insulator 55 used at the bottom of the feedthrough assembly serves as both a chemical and electrical insulator. It is further noted that a plastic insulator cannot be used in cases in which welding of feedthrough assembly components is required, since the heat generated during the welding process could cause a plastic insulator to melt, thereby destroying the insulator and its insulating properties.

The feedthrough pin 58 may be constructed from Nb, Ti, Mo, or Ta. The sealing glass 52 maybe 9013 glass, CABAL-12, or Ta-23 glass. The ferrule 50 may be constructed from MP-35N, 304L stainless steel, titanium 6-4, or some other suitable ferrule material for organic electrolyte lithium batteries.

Figure 12A:
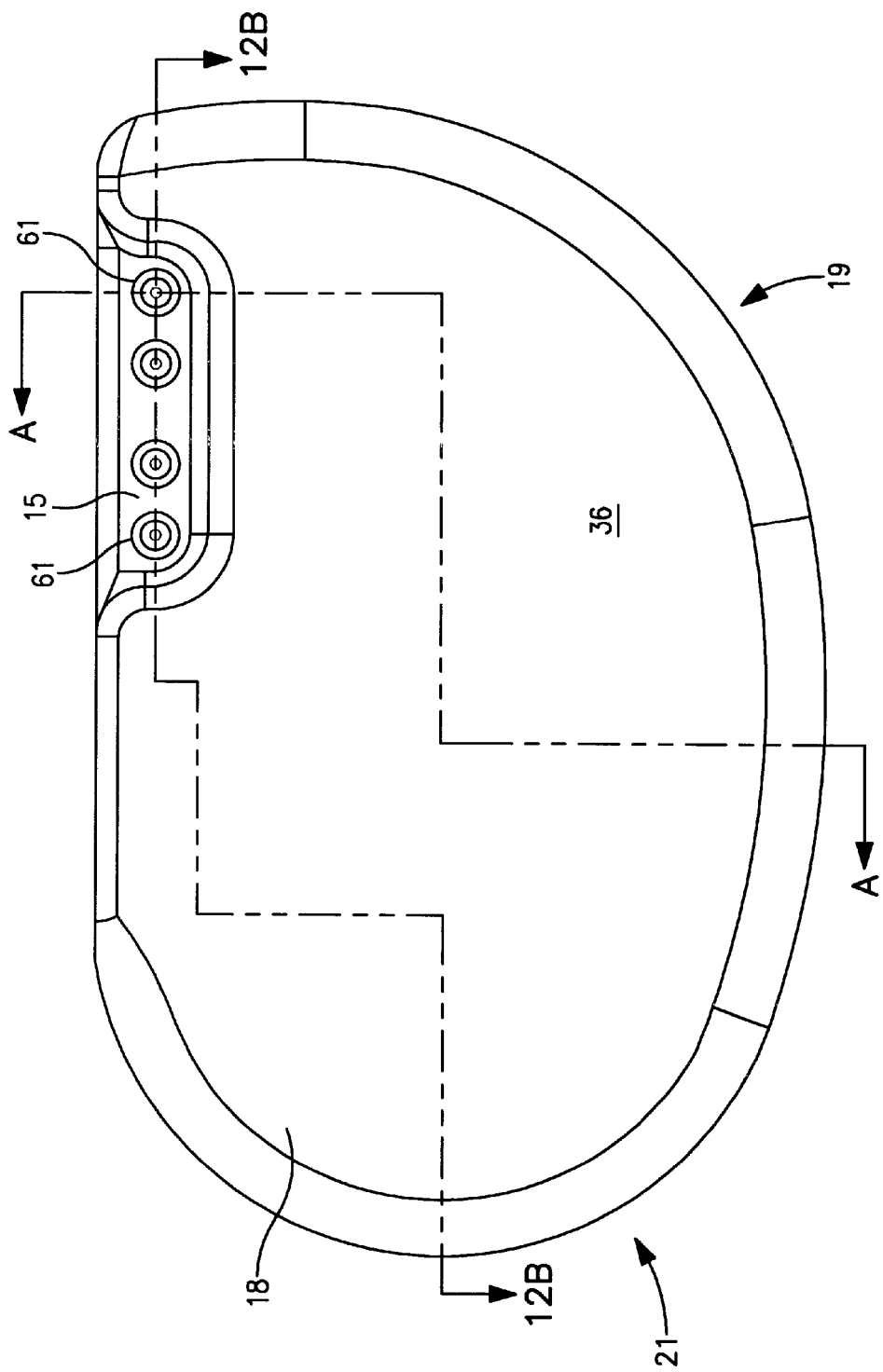
Figure 12B:
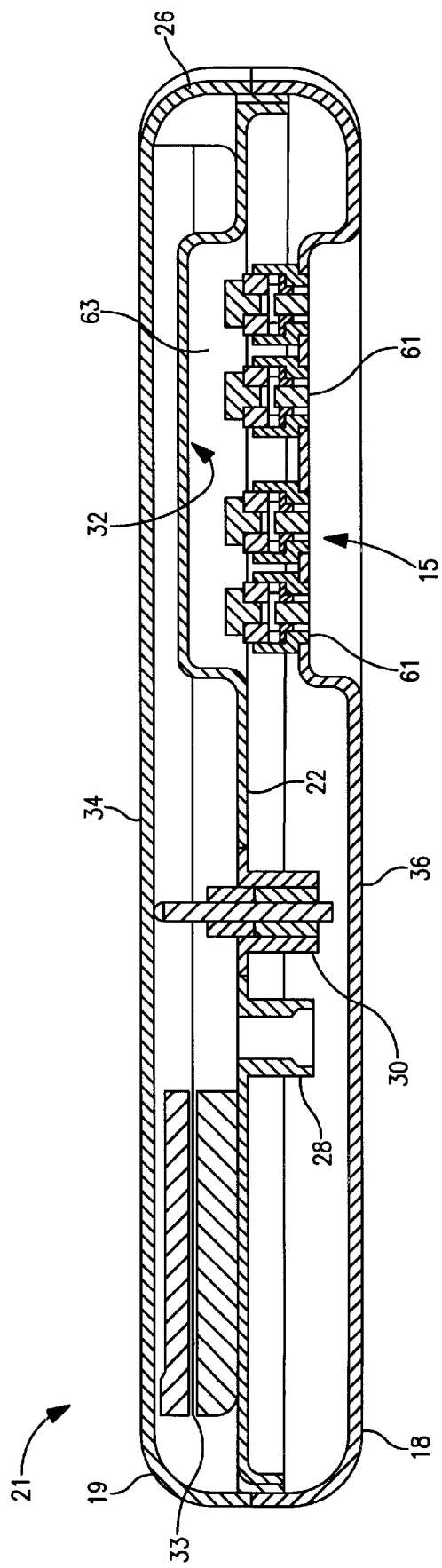

Turning now to FIG. 12, there is illustrated various views of a complete implantable medical device 21 which includes an IMD shield section 18 welded to a battery section 19, as is shown generally in FIG. 2. FIG. 12B is a cross-sectional view of FIG. 12A taken through section B—B. FIG. 12C is a cross-section of FIG. 12A taken through section A—A. FIG. 12D is an exploded view of the dashed circled portion of FIG. 12C. The implantable medical device 21 illustrated in FIG. 12 is shown to have a generally D-shaped or kidney configuration, it being understood that IMD 21 may take on other shapes.

Importantly, and as discussed previously, a flat electrochemical cell disposed in IMD 21 according to the present invention may advantageously be shaped to follow a simple or complex contour of the IMD housing. As such, complex curves, including scalloped and other high-radius curved portions, may be advantageously accommodated.

Moreover, and as will be described hereinbelow, all or some of the electronics disposed in IMD 21 are preferably supported on a flexible substrate, such as a flexible tape or flexible wiring board, which, like the battery components, may be shaped to maximize the space allocated in an IMD housing having complex curved portions. An electronics and battery packaging methodology according to the principles of the present invention provides for enhanced flexibility when designing the size and shape of an implantable medical device to achieve a wide variety of IMD design objectives.

As best seen in FIG. 12B, implantable medical device 21 includes an IMD shield section 18 and a battery section 19. The battery section 19 includes a hermetically-sealed battery housing 26 defined by a cover 22 and all or a portion of the IMD shield or shell 34 opposing IMD shield or shell 36 of the IMD shield section 18. The IMD shield section 18 includes a recessed region 15 to accommodate one or more IMD device feedthroughs 61. The IMD feedthroughs 61 provide external access to the IMD electronics disposed in the IMD shield section 18.

FIG. 12B further shows containment of the active battery components 33 within the battery housing 26, and also shows the battery feedthrough 30 which provides electrical connectivity between the battery 33 and electronics disposed in IMD shield section 18. Cover 22 of the battery housing 26 includes a corresponding recessed region 32 which provides for a feedthrough clearance area 63. The feedthrough clearance area 63 provides space for connecting the IMD feedthroughs 61 to the flexible substrate supporting the IMD electronics.

Figure 21:
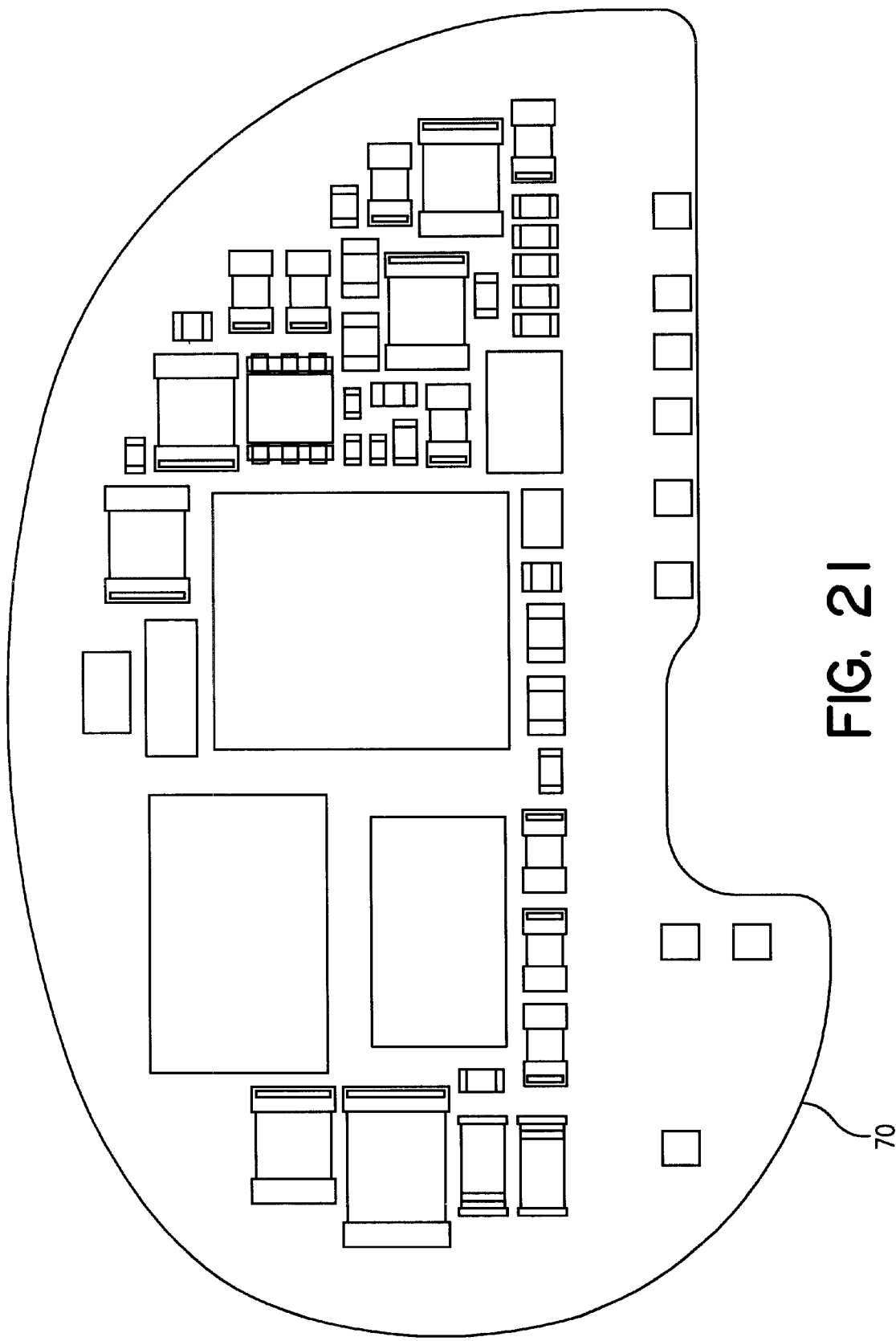
FIG. 21 is an illustration of various electronics populating a flexible wiring substrate of the present invention.

Turning now to FIG. 13, there is illustrated a flexible substrate 70 which supports the implantable medical device electronics, such as those depicted in FIG. 21, for example. FIG. 13 shows a flexible substrate 70 which is situated adjacent the cover 22 of the battery housing. In addition, or alternatively, all or a portion of flexible substrate 70 may be situated proximate the IMD shield (not shown), such as IMD shield 36 shown in FIG. 2.

As can be readily seen in FIG. 13, a significant advantage realized through employment of flexible substrate 70 in comparison to traditional printed wiring boards (PWBs) concerns the conformability of the flexible substrate 70 with respect to the contour of the IMD housing. Moreover, flexible substrate 70 allows the IMD circuitry to conform to contours other than flat surfaces. For example, the flexible substrate 70 may be folded or arranged in any number of non-flat geometries.

Additionally, flexible substrate connections to the terminal block 83, battery, capacitors, and other interfacing electronics can be integrated as part of the flexible circuit, thus eliminating the need for a separate interconnect methodology. The connections to those interfaces can be made by soldering, welding, conductive epoxy attachment or any other suitable attachment methodology. The terminations may either be flat, include a hole which registers over a conductive pin or include a groove that slides against a conductive pin. It will be appreciated that other attachment approaches may also be employed.

The flexible substrate 70 advantageously provides for a lower dielectric constant at a higher dielectric breakdown voltage in comparison to traditional printed wiring boards. In addition, the flexible substrate 70 allows for implantable medical devices to be thinner, yet retain the same number of layers as compared to IMDs employing printed wiring boards. Further, flexible substrate 70 offers a higher thermal stability than printed wiring boards.

In one embodiment, flexible substrate 70 is employed in conjunction with the flat battery shown in FIG. 13 using a single-sided assembly approach. In accordance with this particular implementation, the number of layers required for routing may be cut by one-half, such as from eight layers to four layers. However, double-sided designs may also be employed. The flexible substrate 70 provides for higher interconnect densities in comparison to printed wiring boards, without requiring staggered vias which would otherwise be needed when increasing the routing density of printed wiring boards.

The antenna of an implantable medical device of the present invention may be advantageously enlarged so as to circle the perimeter of the IMD. This allows for a greater range of sensitivity to facilitate IMD telemetry. According to one approach, the antenna may be implemented integrally with the flexible substrate 70, either as a routed antenna or as a coil laminated into the flexible substrate 70.

Flexible substrate 70 includes a cathode connector 74 which connects to the battery cathode via battery feedthrough 30. Flexible substrate 70 further includes an anode connector 76 which is electrically connected to the anode of the battery. Flexible substrate 70 further includes an interconnect 80 which connects with a terminal block 83 of the implantable medical device.

As shown, interconnect 80 represents a continuation of flexible circuit 72 with necessary conductors terminating at appropriate locations for establishing connections to corresponding connectors of the terminal block 83. For example, interconnect 80 includes one or more feedthrough connection locations 72 for establishing electrical connectivity with a corresponding feedthrough connector provided on the IMD shield portion of the IMD housing. Flexible substrate 70 further includes a protection circuit 82 which provides for high current/high voltage protection as between the battery and electronic circuitry of the implantable medical device.

Figure 14:
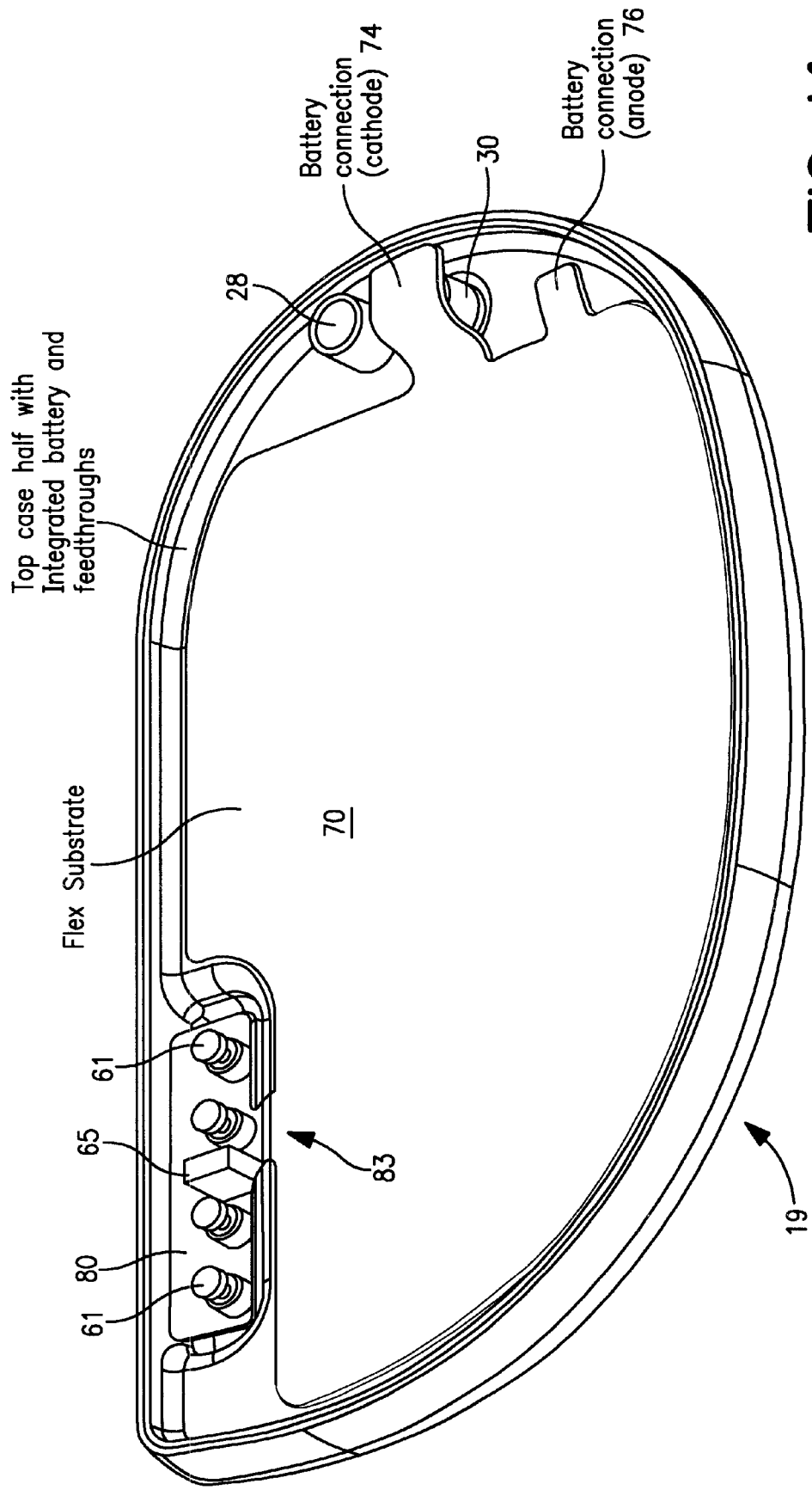
FIG. 14 shows an interconnect strategy for use with a flexible IMD wiring substrate in accordance with another embodiment of the present invention.

FIG. 14 illustrates one embodiment of an interconnect strategy for establishing power and signal connectivity between the internal components of the implantable medical device and external leads, such as pacing leads. According to this embodiment, flexible substrate 70 includes an interconnect 80 which provides connectivity with spring-type connectors of the IMD terminal block 83. According to this embodiment, the IMD feedthrough connectors 61 are of a miniature contact spring configuration which ensures good electrical continuity.

By way of example, the feedthrough connectors 61 may include gold-plated bellows-type contact springs, which are particularly useful in applications where tolerance build-up, vibration, and thermal expansion may become a problem. The contact springs of the feedthrough connector 61 may be manufactured from electro-deposited nickel and gold plated to enhance conductivity. End cups of the connectors may be designed to fit over standard sized pins or into recesses, such that connections to other components may be established without the necessity of soldering. Due to a very low spring rate, force requirements of approximately 0.04 ounces per 0.001 inches of travel are readily achievable. The spring contacts further provide for a minimum of self-inductance with extremely low DC resistance and a minimum of insertion loss.

The contacts 61 may have diameters ranging from 0.037 inches OD (outer diameter) to 0.125 inches OD. The contacts may have either a convex conical or concave conical tip. The contacts may be used individually or in pairs. The unique pairing of a contact with a convex conical tip with a contact having a concave conical receptacle tip allows electrical contacts to be self-aligning as a connection is established. Suitable spring-type contacts 61 are manufactured by Servometer Corporation, Cedar Grove, N.J.

Figure 15:
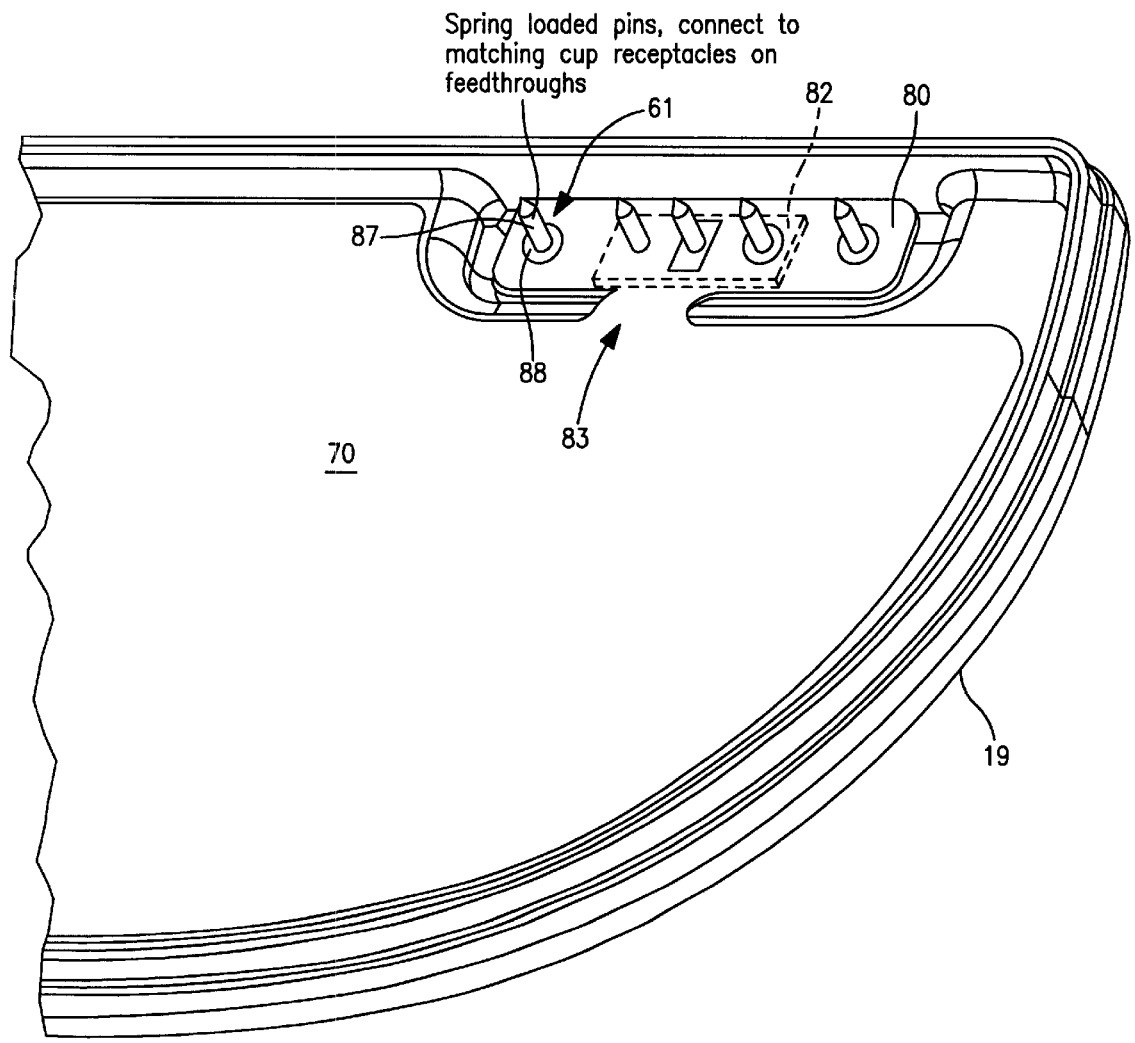
FIG. 15 illustrates yet another interconnect strategy employing a flexible wiring substrate according to an embodiment of the present invention.

FIG. 15 shows another embodiment of an interconnect strategy for establishing electrical connectivity between the terminal block 83 of the IMD electronics and the interconnect 80 of the flexible substrate 70. According to this embodiment, the terminal block 83 includes one or more spring-loaded pins 87. The interconnect 80 of the flexible substrate 70 includes a matching cup receptacle 88 through which the spring-loaded pin 87 passes during installation. The inner diameter of the cup receptacle 88 is matched with the outer diameter of the spring-loaded pin 87 so that good mechanical contact is established therebetween.

Figure 16:
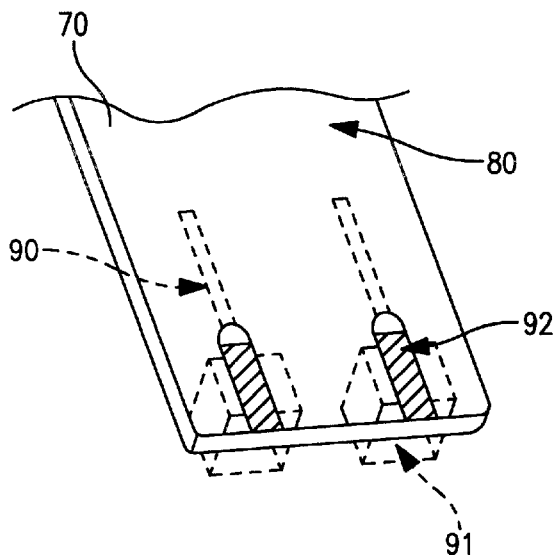
FIGS. 16–18 illustrate various embodiments of an interconnect strategy employing a flexible wiring substrate of the present invention.
Figure 17:
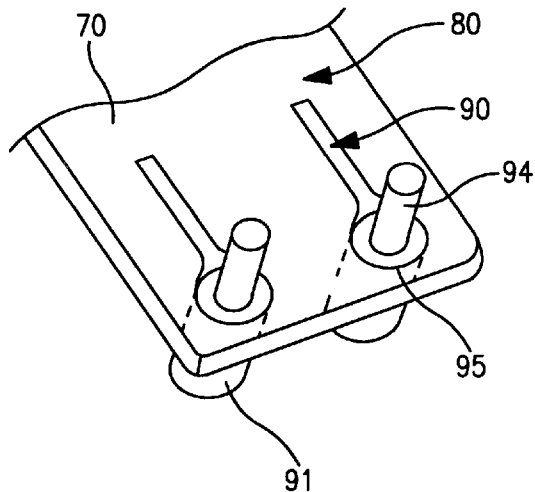
Figure 18:
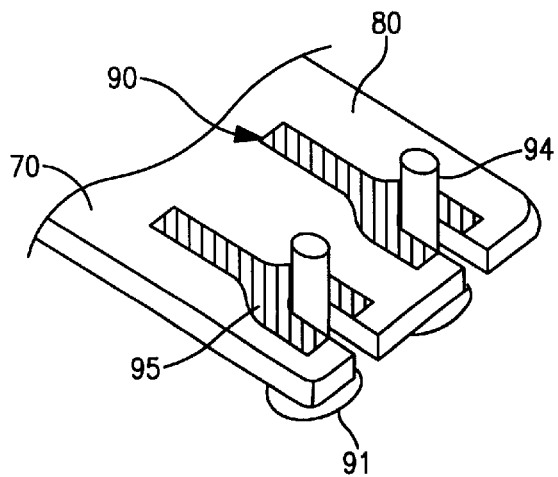

FIGS. 16–18 illustrate three interconnect embodiments for establishing connectivity between the IMD electronics, battery, and pacing leads. FIG. 16 shows a portion of the interconnect 80 of flexible substrate 70 which includes a pair of conductors 90. Each of the conductors 90 are provided on the flexible substrate 70 on the bottom surface of the interconnect 80. A feedthrough terminal or battery connection 91 is shown in phantom below the interconnect 80. The interconnect 80 includes a pad 92 of increased width relative to a width of the conductor 90. When installed, the feedthrough terminal/battery connection 91 makes mechanical contact with pad 92 of interconnect 80.

FIG. 17 illustrates another embodiment of an interconnect strategy in which the flexible interconnect 80 includes a pad 95 provided with a hole. The hole of pad 95 is dimensioned to receive a pin conductor 94 which represents a feedthrough terminal or battery connection. As in the embodiment of FIG. 15, the inner diameter of the hole of pad 95 is dimensioned to mechanically engage the outer diameter of pin 94 so that good electrical contact is established therebetween.

FIG. 18 shows yet another embodiment of an interconnect strategy according to the present invention. Interconnect 80 of flexible substrate 70 includes a U-shaped or C-shaped pad 95 which includes an inner peripheral edge having a curvature that receives the outer diameter of feedthrough pin 94. In this embodiment, interconnect 80 is provided with a slot between the peripheral edge of interconnect 80 and the pad 95. This arrangement provides for slidability during assembly of the interconnect 80 when establishing contact between the flexible substrate 70 and pin conductors 94.

Figure 19:
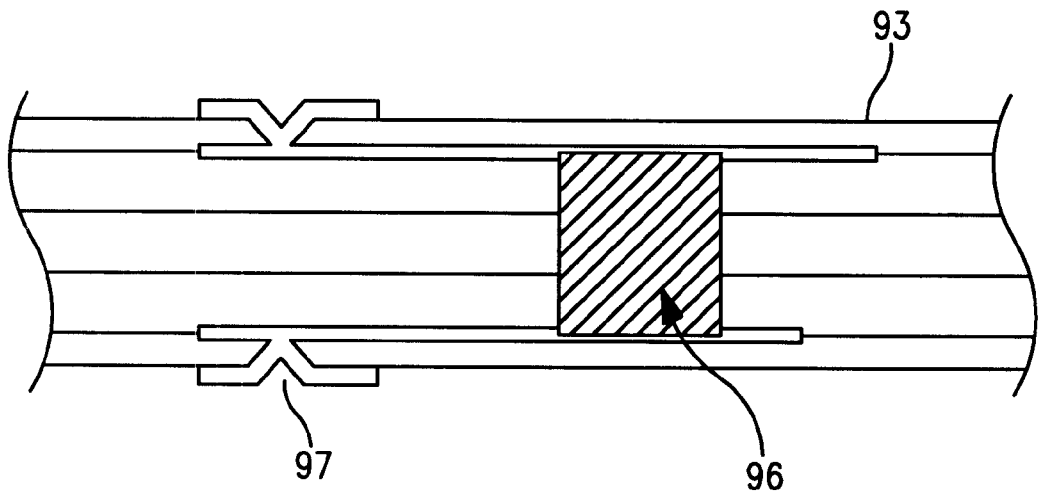
FIG. 19 is a showing of a conventional printed wiring board interconnect via.
Figure 20:
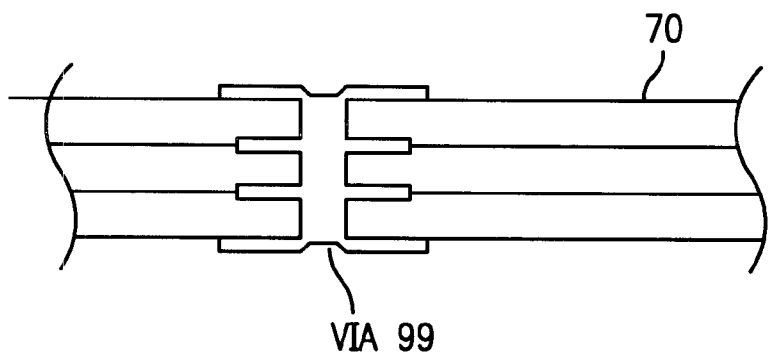
FIG. 20 illustrates a via associated with a flexible wiring substrate of the present invention.

As discussed previously, an advantage of using a flexible substrate 70 according to the present invention concerns the ability to achieve higher interconnect densities by eliminating staggered vias otherwise required in conventional printed wiring board implementations. FIG. 19, for example, illustrates a conventional multi-layer printed wiring board in which a standard via 96 is required to establish connectivity between various printed wiring board layers. Also shown in FIG. 19 is a standard micro-via 97. In contrast to the implementation of FIG. 19, flexible substrate 70 may employ a substantially vertical via 99 which requires substantially less connection area in contrast to that associated with the conventional printed wiring board via of FIG. 19.

Figure 22:
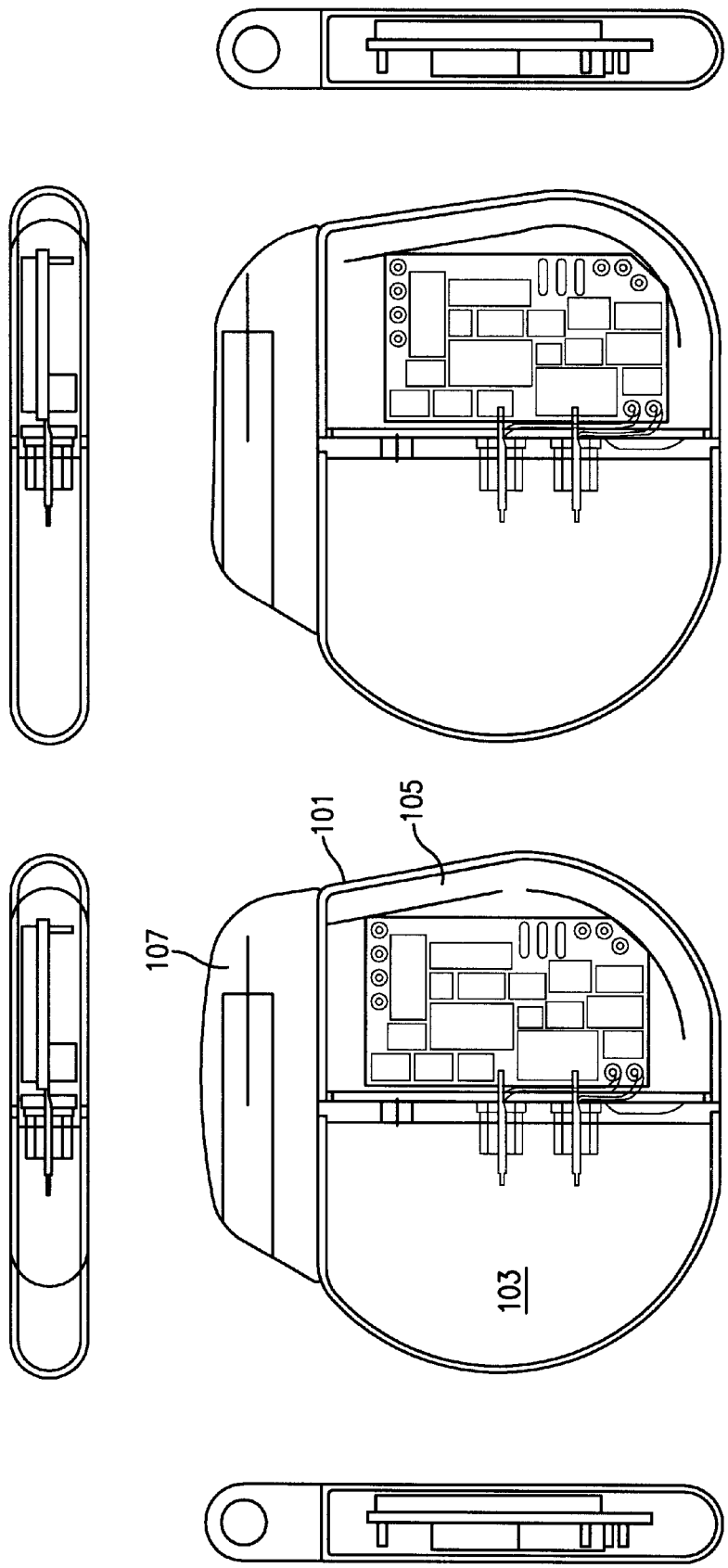
FIG. 22 illustrates another embodiment of an implantable medical device according to the present invention.

FIG. 22 illustrates another embodiment of an implantable medical device which employs a battery compartment 103 separate from the electronics compartment 105. According to this embodiment, the implantable medical device 101 includes three major pieces 103, 105, 107 which snap together to form the completed implantable medical device 101. The electronics compartment 105 is shown to include various implantable medical device electronics which are mounted to a wiring board, which may be a rigid or flexible wiring substrate. FIGS. 4, 11A, 11B, 12, and 12A are corrected per enclosed redline figures.

As was discussed previously, the implantable medical device 21 as shown in the figures may be representative of any of a number of different implantable electronic devices. In certain IMD applications, the polarity of the IMD housing may be an issue. It is believed that a desired IMD housing polarity may be achieved by employing known electronic design principles.

Figure 23A:
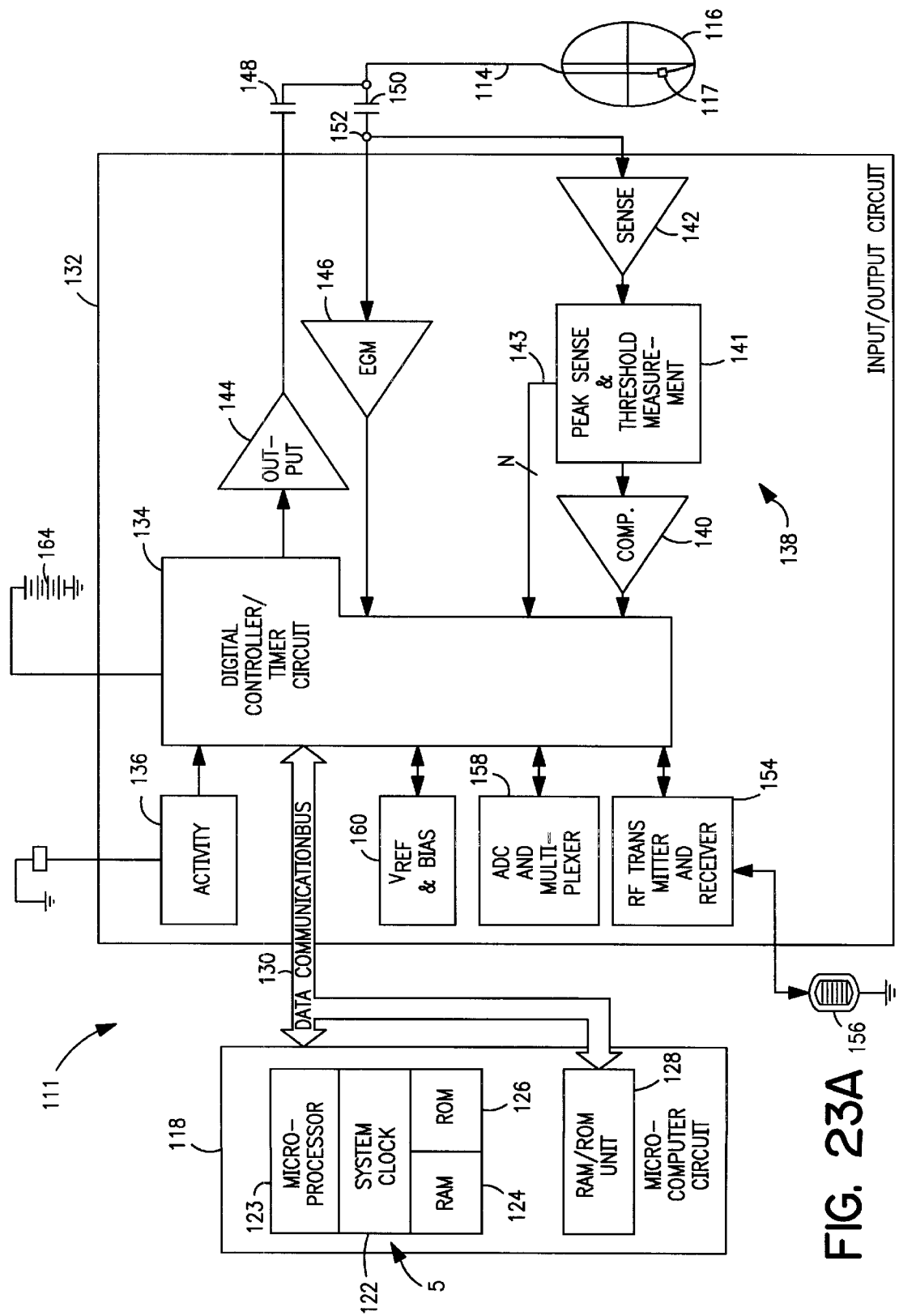
FIGS. 23A–23B illustrate two embodiments of electronic circuitry of an implantable medical device suitable for incorporation in an IMD housing of the present invention.

FIG. 23A is a block diagram illustrating various components of a pacemaker 111 which represents one of many implantable medical devices that may advantageously incorporate a flat liquid electrolyte battery and flexible wiring substrate of the present invention. The electrical components shown in FIG. 23A are preferably powered by a flat liquid electrolyte battery 164 of the type discussed previously hereinabove.

Pacemaker 111 is electrically coupled to the patient's heart 116 by lead 114 Lead 114, which may include one or two conductors, is coupled to a node 152 in the circuitry of pacemaker 111 through input capacitor 150. In the presently disclosed embodiment, an activity sensor 162 provides a sensor output to a processing/amplifying activity circuit 136 of input/output circuit 132. Input/output circuit 132 also contains circuits for interfacing with heart 116, antenna 156, and circuits 144 for application of stimulating pulses to heart 116 to moderate its rate under control of software-implemented algorithms in microcomputer unit 118.

Microcomputer unit 118 comprises on-board circuit 125 which includes microprocessor 120, system clock 122, and on-board RAM 124 and ROM 126. In this illustrative embodiment, off-board circuit 128 comprises a RAM/ROM unit. On-board circuit 125 and off-board circuit 128 are each coupled by a data communication bus 130 to digital controller/timer circuit 134.

In one embodiment, the pacemaker 111 is programmable by means of an external programming unit (not shown). One such programmer suitable for the purposes of the present invention is the commercially available Medtronic Model 9790 programmer. The programmer is a microprocessor-based device which provides a series of encoded signals to pacemaker 111 by means of a programming head which transmits radio frequency (RF) encoded signals to pacemaker 111 according to a telemetry system such as that described in U.S. Pat. No. 5,312,453 to Shelton et al. and U.S. Pat. No. 5,127,404 issued to Wyborny et al., the disclosures of which are hereby incorporated by reference herein in their respective entireties.

Antenna 156 is connected to input/output circuit 132 to permit uplink/downlink telemetry through RF transmitter and receiver unit 154. Unit 154 may correspond to the telemetry and program logic disclosed in U.S. Pat. No. 4,556,063 issued to Thompson et al., hereby incorporated by reference herein in its entirety, or to that disclosed in the above-referenced Wyborny et al. patent.

Voltage reference ($V_{REF}$) and bias circuit 160 generates a stable voltage reference and bias current for the analog circuits of input/output circuit 132. Analog-to-digital converter (ADC) and multiplexer unit 158 digitizes analog signals and voltages to provide "real-time" telemetry intracardiac signals and battery end-of-life (EOL) replacement functions.

Operating commands for controlling the timing of pacemaker 111 are coupled by data bus 130 to digital controller/timer circuit 134, where digital timers and counters establish the overall escape interval of the pacemaker as well as various refractory, blanking, and other timing windows for controlling the operation of the peripheral components disposed within input/output circuit 132. Digital controller/timer circuit 134 is preferably coupled to sensing circuitry 138, including sense amplifier 142, peak sense and threshold measurement unit 141, and comparator/threshold detector 140.

Sense amplifier 142 amplifies sensed electrocardiac signals and provides an amplified signal to peak sense and threshold measurement circuitry 141. Circuitry 141, in turn, provides an indication of peak sensed voltages and measured sense amplifier threshold voltages on path 143 to digital controller/timer circuit 134. An amplified sense amplifier signal is then provided to comparator/threshold detector 140. Sense amplifier 142 may correspond to that disclosed in U.S. Pat. No. 4,379,459 to Stein, which is hereby incorporated by reference herein in its entirety.

Circuit 134 is further preferably coupled to electrogram (EGM) amplifier 146 for receiving amplified and processed signals sensed by an electrode disposed on lead 114. The electrogram signal provided by EGM amplifier 146 is employed when the implanted device is being interrogated by an external programmer (not shown) to transmit, by uplink telemetry according to the present invention, a representation of an analog electrogram of the patient's electrical heart activity. Such functionality is, for example, shown in previously referenced U.S. Pat. No. 4,556,063.

Output pulse generator 144 provides pacing stimuli to the patient's heart 116 through coupling capacitor 148 in response to a pacing trigger signal provided by digital controller/timer circuit 134. For example, each time the escape interval times out, an externally transmitted pacing command is received, or such commands are received in response to other stored commands as is well known in pacing art. Output amplifier 144, for example, may correspond generally to the output amplifier disclosed in U.S. Pat. No. 4,476,868 to Thompson, also incorporated by reference herein in its entirety.

Figure 23B:
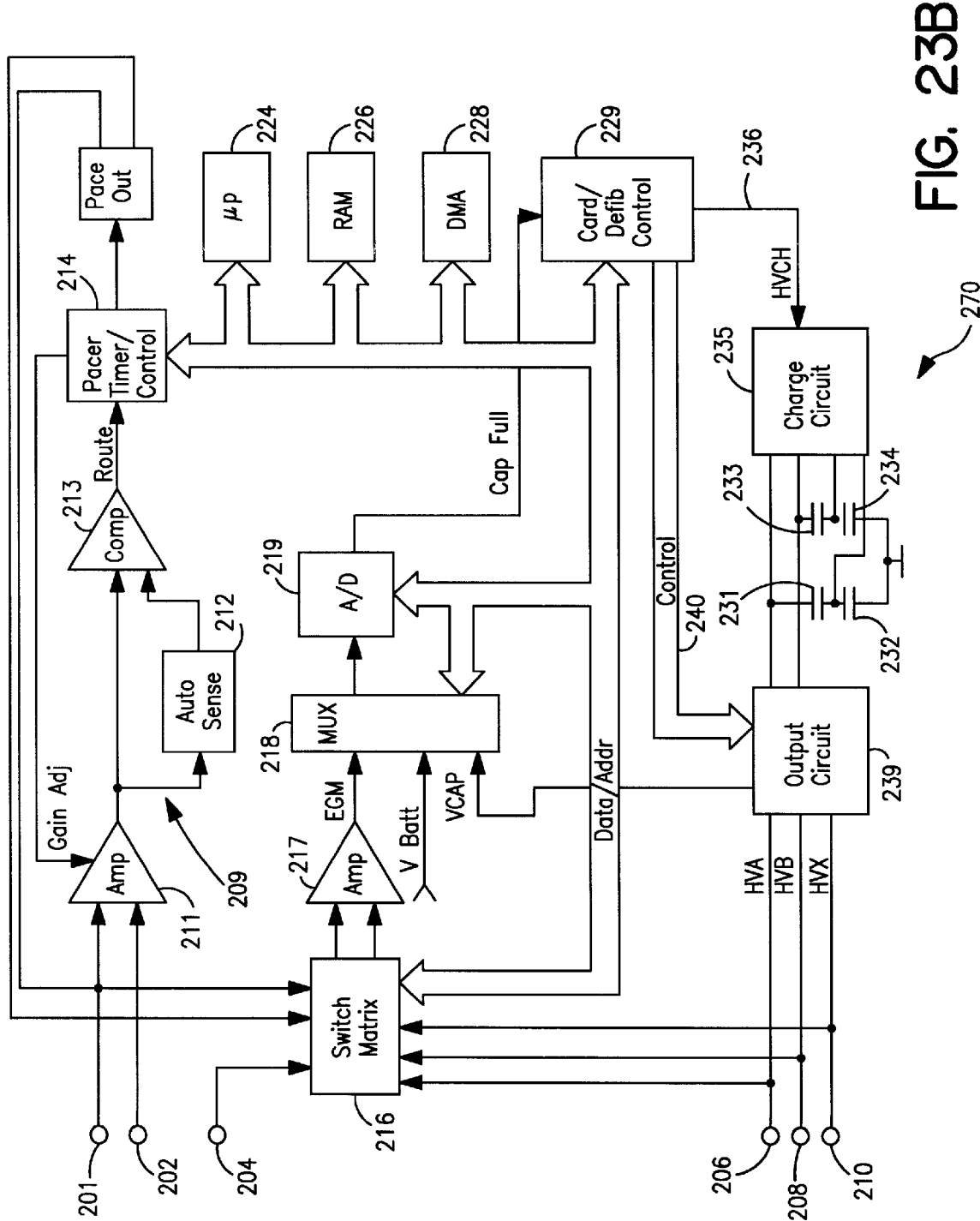

FIG. 23B is a functional schematic diagram which shows an implantable pacemaker/cardioverter/defibrillator (PCD) 270 which represents another one of many implantable medical devices that may advantageously incorporate a flat liquid electrolyte battery and flexible wiring substrate of the present invention. Implantable pacemaker/cardioverter/defibrillator (PCD) 270 may have a structure and functionality similar to that disclosed in U.S. Pat. No. 5,447,519, which is incorporated by reference herein in its entirety.

The PCD device 270 is provided with six electrodes 201, 202, 204, 206, 208, and 210. For example, electrodes 201 and 202 may be a pair of closely-spaced electrodes located in the ventricle. Electrode 204 may correspond to a remote, indifferent electrode located on the housing of the implantable PCD 270. Electrodes 206, 208, and 210 may correspond to large surface area defibrillation electrodes located on device leads or to epicardial electrodes.

Electrodes 201 and 202 are connected to detector circuit 209 which includes band pass filtered amplifier 211, auto-threshold circuit 212, which provides an adjustable sensing threshold, and comparator 213. A signal is generated by the comparator 213 whenever the signal sensed between electrodes 201 and 202 exceeds the sensing threshold defined by auto-threshold circuit 212. Further, the gain of amplifier 211 is adjusted by pacer timing and control circuitry 214. The sense signal, for example, is used to set the timing windows and to align successive waveshape data for morphology detection purposes. For example, the sense event signal may be routed through the pacer/timer control circuit 214 on data bus 215 to processor 224 and may act as an interrupt for processor 224 such that a particular routine of operations is commenced by processor 224.

Switch matrix 216 is used to select available electrodes under the control of processor 224 via data/address bus 215, such that the selection includes two electrodes employed as a far field electrode pair in conjunction with a tachycardia/fibrillation discrimination function. Far field EGM signals from the selected electrodes are passed through band pass amplifier 217 and into multiplexer 218, where they are converted to multi-bit digital data signals by A/D converter 219 for storage in random access memory 226 under the control of direct memory address circuitry 228.

The processor 224 may perform various morphology detection functions. For example, such detection functions may be indicative of tachycardia or fibrillation, or various other functions may be performed as set out in numerous references including any of the references incorporated herein by reference and others with regard to implantable PCDs.

The remainder of the device 270 of FIG. 23B is dedicated to the provision of cardiac pacing, cardioversion, and defibrillation therapies. The pacer timing/control circuit 214 includes programmable digital counters that control the basic timing intervals associated with cardiac pacing. Further, under control of processor 224, pacer timing/control circuit 214 also determines the amplitude of such cardiac pacing pulses.

In the event that a tachyarrhythmia is detected, and an anti-tachyarrhythmia pacing therapy is desired, appropriate timing intervals for controlling generation of pacing therapies are loaded from processor 224 into pacer timing and control circuitry 214. Similarly, in the event that generation of a cardioversion or defibrillation pulse is required, processor 224 employs the timing and control circuitry 214 to control timing of such cardioversion and defibrillation pulses.

In response to detection of fibrillation or a tachycardia requiring a cardioversion pulse, processor 224 activates cardioversion/defibrillation control circuitry 229, which initiates charging of the high voltage capacitors 231–234 via charging circuit 235 under the control of high voltage charging line 236. Thereafter, delivery and timing of the defibrillation or cardioversion pulse is controlled by pacer timing/control circuitry 214. One embodiment of an appropriate system for delivering and synchronizing cardioversion and defibrillation pulses, and controlling the timing functions related thereto, is disclosed in greater detail in U.S. Pat. No. 5,188,105 to Keimel, which is incorporated herein by reference in its entirety.

Other circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,374,817 to Engle et al., all of which are incorporated herein by reference in their respective entireties. Further, known circuitry for controlling the timing-and generation of anti-tachycardia pacing pulses is described in U.S. Pat. No. 4,577,633 to Berkovitz et al., U.S. Pat. No. 4,880,005 to Pless et al., U.S. Pat. No. 4,726,380 to Vollmann et al., and U.S. Pat. No. 4,587,970 to Holley et al., all of which are incorporated herein by reference in their respective entireties.

It is understood that this diagram is an illustration of an exemplary type of device in which the invention may find application, and is not intended to limit the scope of the present invention. Other implantable medical devices, such as those described previously, having functional organizations wherein the present invention may be useful, may also be modified to incorporate an integral IMD battery housing for containing a flat liquid electrolyte battery and flexible wiring substrate in accordance with the present invention. For example, the present invention is also believed to be useful in conjunction with implantable pacemakers/cardioverters/defibrillators as disclosed in U.S. Pat. No. 4,548,209 to Wielders, et al.; U.S. Pat. No. 4,693,253 to Adams et al.; U.S. Pat. No. 4,830,006 to Haluska et al.; and U.S. Pat. No. 4,949,730 to Pless et al.; all of which are incorporated herein by reference in their respective entireties.

The foregoing description of the various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A selectively deformable housing assembly for an implantable medical device, comprising:

a housing comprising a first shell and a second shell, the first and second shells comprising an inner surface and an outer surface, respectively, the outer surfaces of the first and second shells comprising a material compatible with body fluids;

a battery enclosure comprising a cover and all or a portion of the first shell of the housing assembly, the cover of the battery enclosure disposed between the inner surfaces of the first and second shells, wherein said cover has a greater thickness dimension or a higher modulus of elasticity than the first shell and an insulated electrical conductor sealingly coupled therethrough;

an electrochemical battery cell including an anode member, a cathode pellet and a liquid electrolyte disposed in the battery enclosure;

an operable electronic circuit electrically coupled to the electrochemical battery cell, electrically coupled to a medical electrical lead, and wherein said operable electronic circuit is mechanically coupled between the inner surface of the second shell and the cover of the battery enclosure and a majority of the operable electronic circuit is coupled to a deformable, flexible circuit substrate; and a hermetic seal isolating the battery enclosure.

2. The deformable housing assembly of claim 1, wherein the thickness dimension of the cover is approximately double the thickness of the first shell.

3. The deformable housing assembly of claim 1, wherein the first and second shells are fabricated from surgical Grade I Titanium.

4. The deformable housing assembly of claim 3, wherein the electrochemical battery cell further includes a lithium anode, a cathode pellet with Li/CSVO/$CF_x$ chemistry and a liquid electrolyte of type 1M $LiBF_y$ in GBL/DME.

5. The deformable housing assembly of claim 4, wherein the liquid electrolyte is type 1 N $LiAsF_6$ in PC/DME with Li/CSOV chemistry.

6. The deformable housing assembly of claim 5, wherein the liquid electrolyte is a one of the following: $Li/MnO_2$, Li/SVO, Li/$CF_x$, or Li/SVO—$CF_x$.

7. The deformable housing assembly of claim 1, further including a feedthrough assembly coupling the battery enclosure to the operable electronic circuit, the feedthrough assembly disposed in a hermetically sealed aperture of the cover and further including a ferrule and a feedthrough pin electrically isolated from each other by a sealing glass.

8. The deformable housing assembly of claim 7, wherein the feedthrough pin is constructed from a one of the following materials: Nb, Ni, Ti, Mo, or Ta;

wherein the sealing glass is a one of the following: 9013 glass, CABAL-12, or Ta-23 glass; and wherein the ferrule is constructed from a one of the following materials: MP-35N, 304L stainless steel or titanium 6-4.

9. The deformable housing assembly of claim 1, further comprising:

an antenna coupled to the deformable, flexible substrate.

10. The deformable housing assembly of claim 9, wherein the antenna is embedded into the deformable, flexible substrate.

11. The deformable housing assembly of claim 1, wherein the implantable medical device is one of the following: a pacemaker, a monitoring device, a nerve stimulator, a pacemaker/cardioverter/defibrillator, or an implantable cardioverter/defibrillator.

12. The deformable housing assembly of claim 1, wherein the cover has regions of different elevation and at least one of the regions defines a recessed region between the cover and the second shell.

13. The deformable housing assembly of claim 1, wherein the battery enclosure has a maximum thickness of approximately 0.135 inches.

14. The deformable housing assembly of claim 1, wherein the housing is further defined by a perimeter, the perimeter having a significant curvilinear portion.

15. A selectively deformable housing assembly for an implantable medical device, comprising:

a housing comprising a first shell and a second shell, the first and second shells comprising an inner surface and an outer surface, respectively, the outer surfaces of the first and second shells comprising a material compatible with body fluids, the first shell comprising a substantially straight peripheral wall portion;

a battery enclosure comprising a cover and all or a portion of the first shell of the housing assembly, the cover of the battery enclosure disposed between the inner surfaces of the first and second shells, wherein said cover comprises a coined edge and has a greater thickness dimension or a higher modulus of elasticity than the first shell, and an insulated electrical conductor sealingly coupled therethrough;

an electrochemical battery cell including an anode member, a cathode pellet and a liquid electrolyte disposed in the battery enclosure;

an operable electronic circuit electrically coupled to the electrochemical battery cell, electrically coupled to a medical electrical lead, and wherein said operable electronic circuit is mechanically coupled between the inner surface of the second shell and the cover of the battery enclosure and a majority of the operable electronic circuit is coupled to a deformable, flexible circuit substrate; and a hermetic seal comprising a butt weld joint between the coined edge of the cover and the substantially straight peripheral wall portion of the first shell.

16. A selectively deformable housing assembly for an implantable medical device, comprising:

a housing comprising a first shell and a second shell, the first and second shells comprising an inner surface and an outer surface, respectively, the outer surfaces of the first and second shells comprising a material compatible with body fluids, the first shell comprising a spanked edge;

a battery enclosure comprising a cover and all or a portion of the first shell of the housing assembly, the cover of the battery enclosure disposed between the inner surfaces of the first and second shells, wherein the cover comprises a peripheral edge and has a greater thickness dimension or a higher modulus of elasticity than the first shell, and an insulated electrical conductor sealingly coupled therethrough;

an electrochemical battery cell including an anode member, a cathode pellet and a liquid electrolyte disposed in the battery enclosure;

an operable electronic circuit electrically coupled to the electrochemical battery cell, electrically coupled to a medical electrical lead, and wherein said operable electronic circuit is mechanically coupled between the inner surface of the second shell and the cover of the battery enclosure and a majority of the operable electronic circuit is coupled to a deformable, flexible circuit substrate; and a hermetic seal comprising a spank weld joint between the peripheral edge of the cover and the spanked edge of the first shell.

17. The deformable housing assembly of claim 16, wherein the first shell further comprises a first substantially straight peripheral wall portion and a second substantially straight peripheral wall portion adjacent the first substantially straight peripheral wall portion and being offset relative to the first substantially straight peripheral wall portion, the first substantially peripheral wall portion defining a ledge which the peripheral edge of the cover engages.

18. A selectively deformable housing assembly for an implantable medical device, comprising:

a housing comprising a first shell and a second shell, the first and second shells comprising an inner surface and an outer surface, respectively, the outer surfaces of the first and second shells comprising a material compatible with body fluids, the first shell comprising a first substantially straight peripheral wall portion and a second substantially straight peripheral wall portion adjacent the first substantially straight peripheral wall portion and being offset relative to the first substantially straight peripheral wall portion;

a battery enclosure comprising a cover and all or a portion of the first shell of the housing assembly, the cover of the battery enclosure disposed between the inner surfaces of the first and second shells, wherein the cover comprises a substantially straight peripheral wall portion and has a greater thickness dimension or a higher modulus of elasticity than the first shell, and an insulated electrical conductor sealingly coupled therethrough;

an electrochemical battery cell including an anode member, a cathode pellet and a liquid electrolyte disposed in the battery enclosure;

an operable electronic circuit electrically coupled to the electrochemical battery cell, electrically coupled to a medical electrical lead, and wherein said operable electronic circuit is mechanically coupled between the inner surface of the second shell and the cover of the battery enclosure and a majority of the operable electronic circuit is coupled to a deformable, flexible circuit substrate; and a hermetic seal comprising a standing edge weld joint between the substantially straight peripheral wall portion of the cover and either the first or the second substantially straight peripheral wall portions of the first shell.

* * * * *